(12) United States Patent
Uesugi et al.

(10) Patent No.: US 10,542,873 B2
(45) Date of Patent: Jan. 28, 2020

(54) ENDOTRACHEAL INTUBATION SUPPORT INSTRUMENT

(71) Applicant: SENKO MEDICAL INSTRUMENT Mfg. Co., Ltd., Tokyo (JP)

(72) Inventors: Takanobu Uesugi, Osaka (JP); Mitsuru Chiba, Tokyo (JP); Yasushi Honda, Tokyo (JP); Jun Suzuki, Tokyo (JP)

(73) Assignee: SENKO MEDICAL INSTRUMENT MFG. CO., LTD., Tokyo (JP)

( * ) Notice: Subject to any disclaimer, the term of this patent is extended or adjusted under 35 U.S.C. 154(b) by 343 days.

(21) Appl. No.: 15/501,738

(22) PCT Filed: Aug. 7, 2015

(86) PCT No.: PCT/JP2015/072556
§ 371 (c)(1),
(2) Date: Feb. 3, 2017

(87) PCT Pub. No.: WO2016/021724
PCT Pub. Date: Feb. 11, 2016

(65) Prior Publication Data
US 2017/0224200 A1     Aug. 10, 2017

(30) Foreign Application Priority Data
Aug. 7, 2014   (JP) ................................. 2014-161671

(51) Int. Cl.
*A61B 1/00* (2006.01)
*A61B 1/015* (2006.01)
(Continued)

(52) U.S. Cl.
CPC .......... *A61B 1/00147* (2013.01); *A61B 1/015* (2013.01); *A61B 1/2676* (2013.01);
(Continued)

(58) Field of Classification Search
CPC ..... A61B 1/00147; A61B 1/015; A61B 1/267; A61B 1/2676; A61M 16/0488;
(Continued)

(56) References Cited

U.S. PATENT DOCUMENTS 5,038,766 A   8/1991  Parker
5,174,283 A   12/1992 Parker
(Continued)

FOREIGN PATENT DOCUMENTS

JP   05-501660 A    4/1993
JP   2001-515388 A  9/2001
(Continued)

OTHER PUBLICATIONS

International Search Report dated Oct. 27, 2015 for the corresponding PCT Application No. PCT/JP2015/072556.
(Continued)

*Primary Examiner* — Nilay J Shah
(74) *Attorney, Agent, or Firm* — Leason Ellis LLP

(57) ABSTRACT

Endotracheal intubation support instrument comprises: a main body section having flexibility; a handle section and a blade section extending from both sides of the main body section respectively; and a U-shaped groove running through the main body section from the handle section to the blade section and allowing a flexible tube of a bronchial fiber to come in and out freely. The blade section comprises: a flap for subsuming all or a part of a larynx of a patient; and a lifting body having, on each bank of the U-shape groove, a first protruding portion allowed to contact with a peripheral portion of an epiglottis of the patient and a second protruding portion provided next to a main body section side of the first protruding portion and allowed to contact with a peripheral portion of a glossal root of the patient.

19 Claims, 35 Drawing Sheets

(51) Int. Cl.
    *A61B 1/267* (2006.01)
    *A61M 16/04* (2006.01)

(52) U.S. Cl.
    CPC ..... *A61M 16/0488* (2013.01); *A61B 1/00154* (2013.01); *A61B 1/267* (2013.01); *A61M 16/0463* (2013.01); *A61M 2205/0216* (2013.01); *A61M 2205/0222* (2013.01); *A61M 2210/0656* (2013.01)

(58) Field of Classification Search
    CPC .......... A61M 16/0497; A61M 16/0465; A61M 16/04; A61M 16/0402; A61M 16/0463; A61M 2210/06; A61M 2210/0625; A61M 2210/065; A61M 2210/0656
    See application file for complete search history.

(56) References Cited

U.S. PATENT DOCUMENTS

| | | |
|---|---|---|
| 5,339,805 A | 8/1994 | Parker |
| 5,713,868 A * | 2/1998 | Fussman ............... A61M 25/06 604/164.01 |
| 5,743,254 A | 4/1998 | Parker |
| 6,119,695 A | 9/2000 | Augustine et al. |
| 6,338,343 B1 | 1/2002 | Augustine et al. |
| 6,550,475 B1 | 4/2003 | Oldfield |
| 2002/0117171 A1* | 8/2002 | Parker ............... A61M 16/0488 128/200.26 |
| 2011/0120474 A1 | 5/2011 | Daugherty et al. |

FOREIGN PATENT DOCUMENTS

| | | |
|---|---|---|
| JP | 2002-505925 A | 2/2002 |
| JP | 2003-235978 A | 8/2003 |
| JP | 2004-523306 A | 8/2004 |
| WO | WO-91/07201 | 5/1991 |
| WO | WO-98/41137 | 9/1998 |
| WO | WO-98/41272 | 9/1998 |
| WO | WO-99/45990 | 9/1999 |
| WO | WO-00/30706 | 6/2000 |
| WO | WO-02/068033 A | 9/2002 |

OTHER PUBLICATIONS

Extended European Search Report dated Mar. 9, 2018 for the corresponding European Patent Application No. 15829084.1.

* cited by examiner

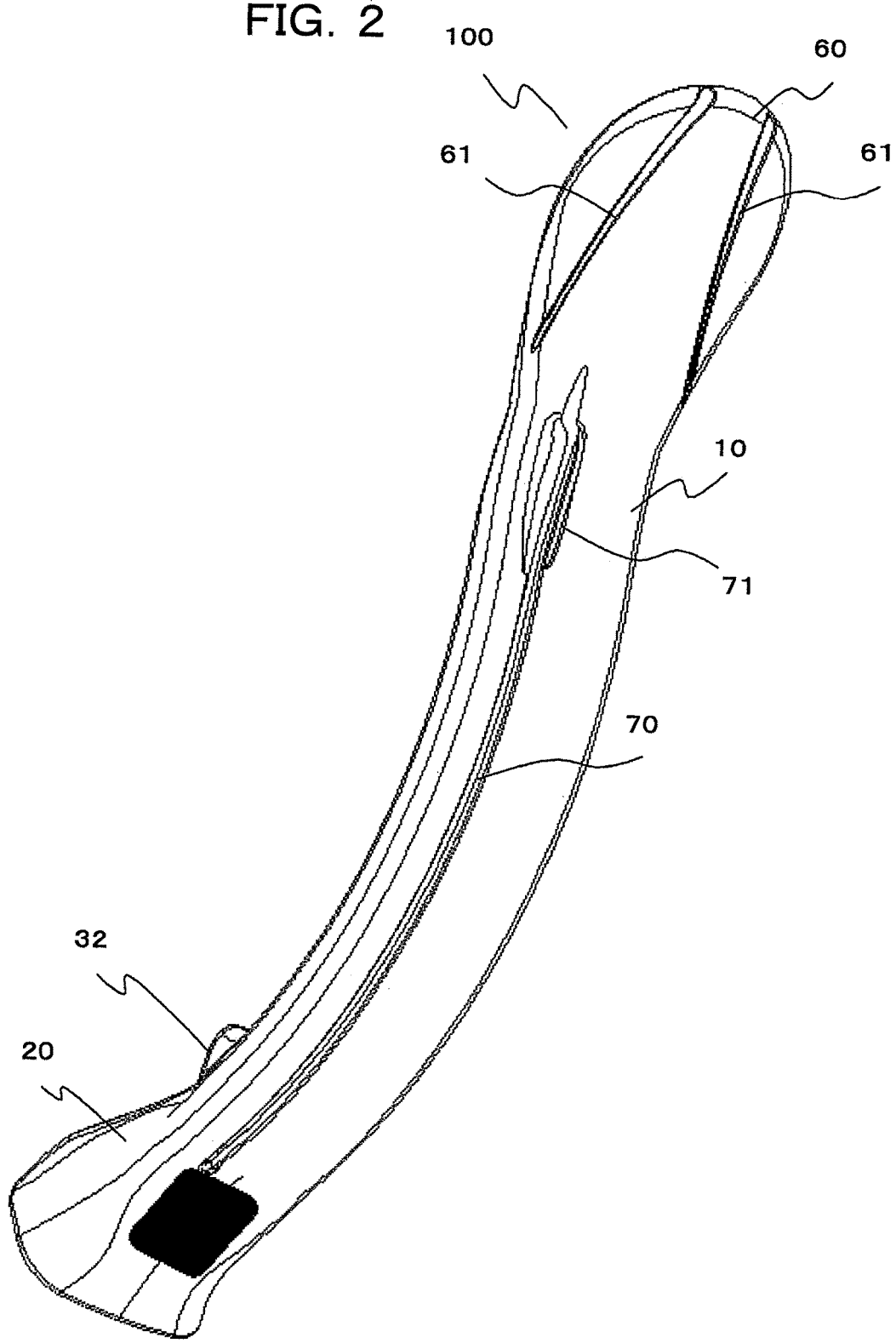

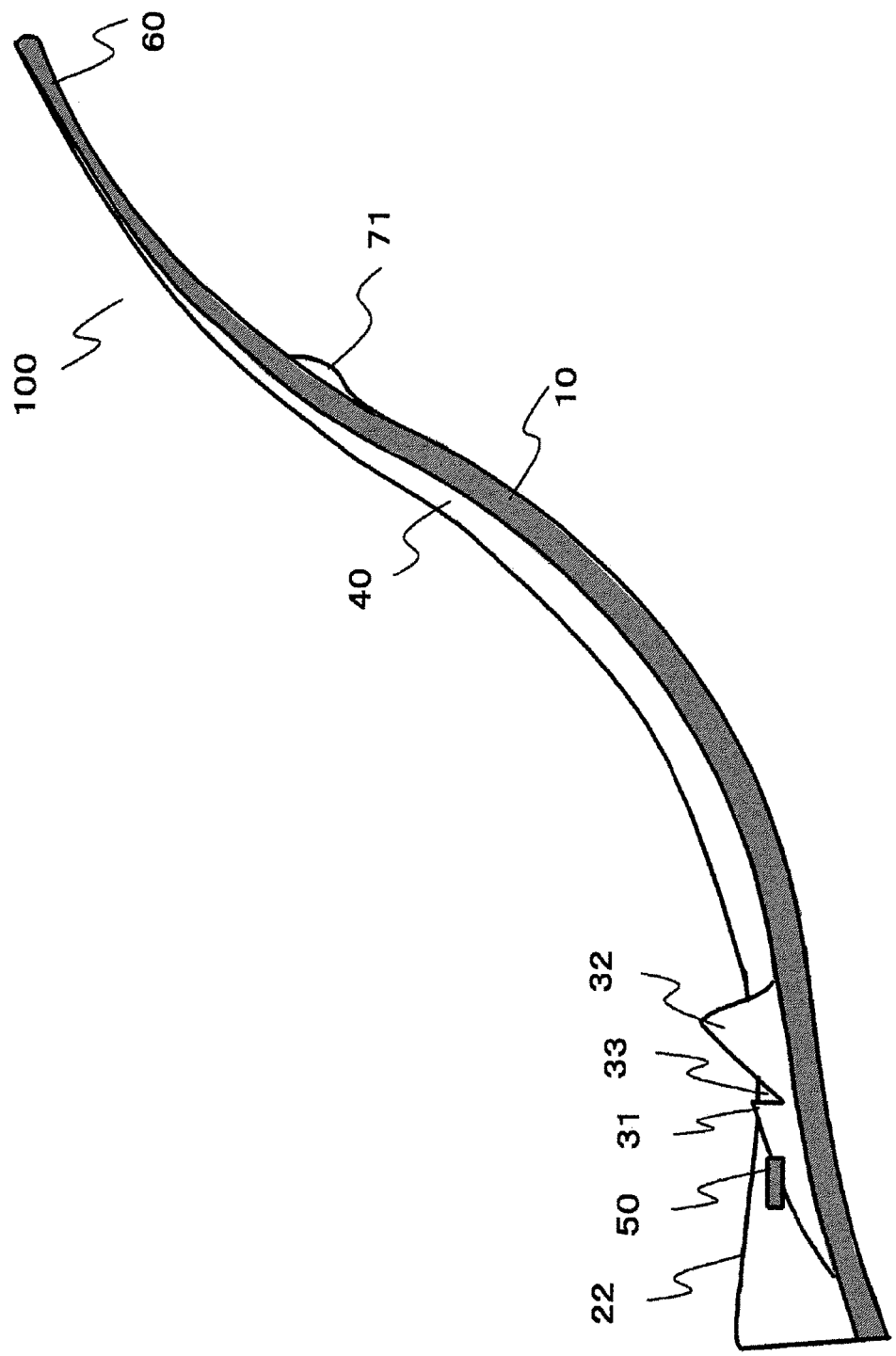

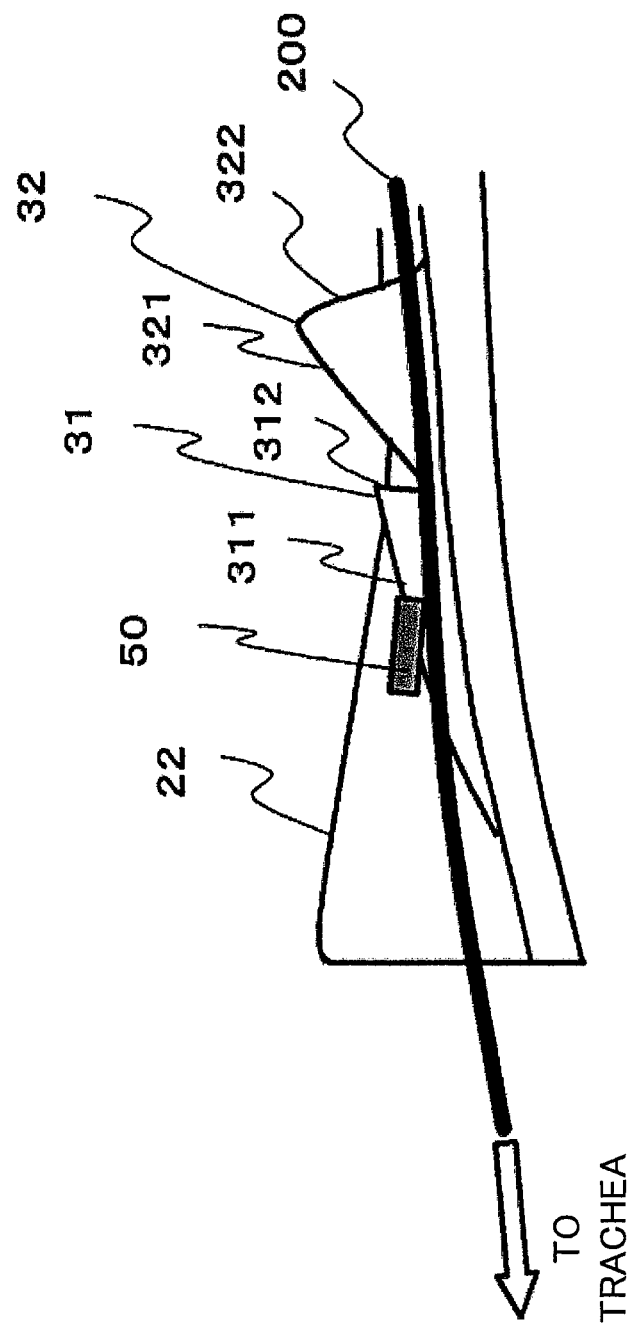

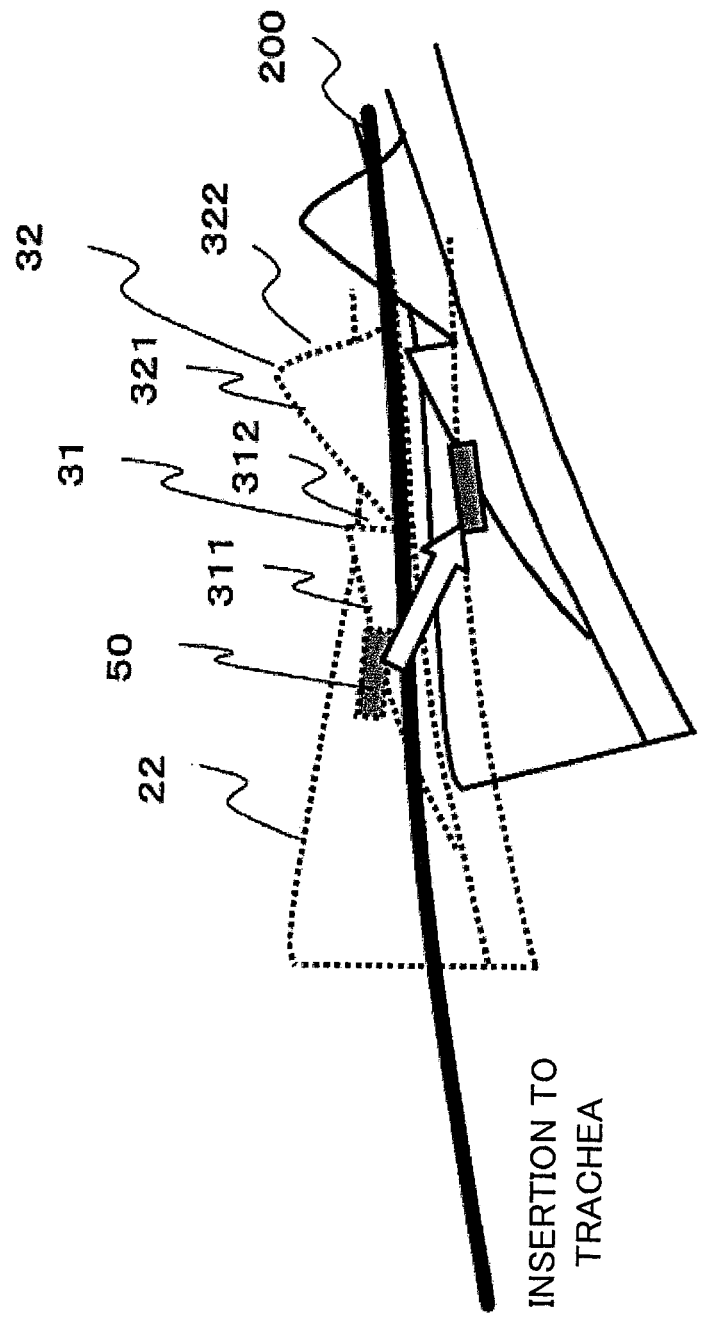

FIG. 20A     (Prior Art)
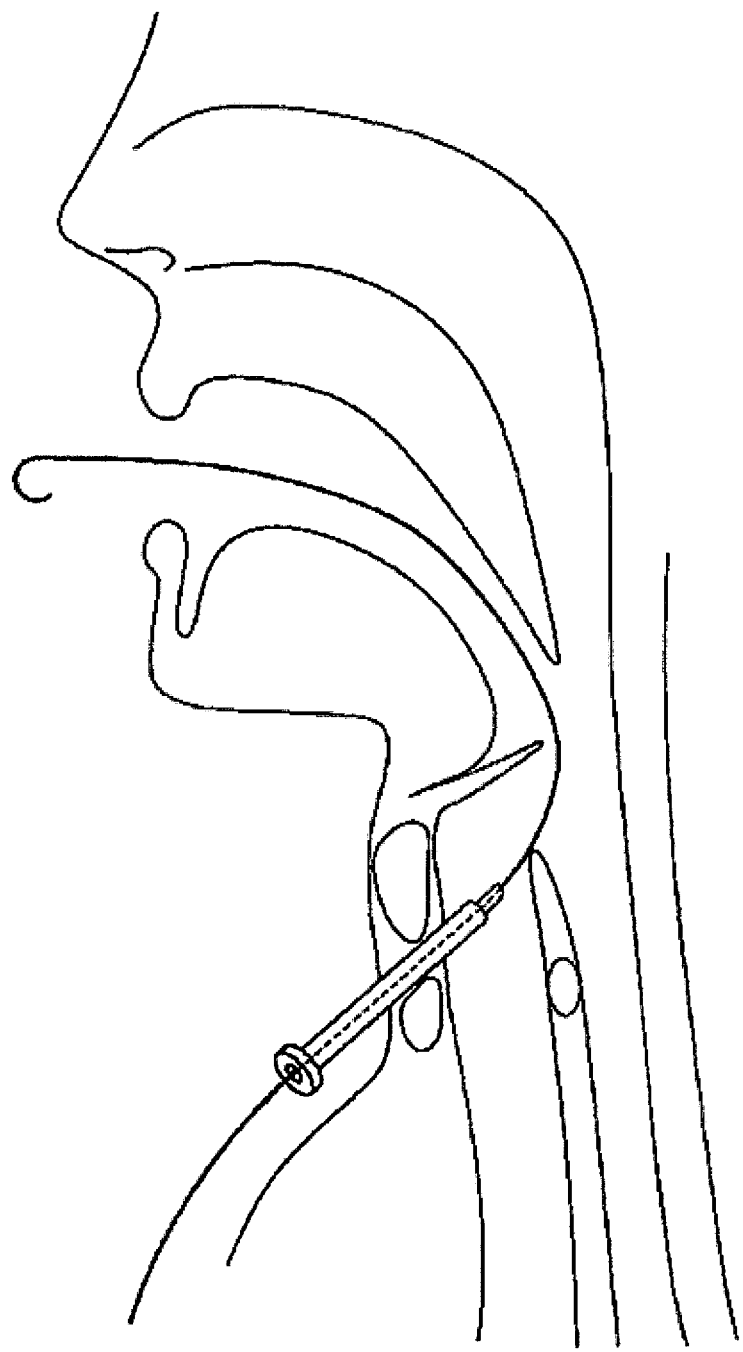

ENDOTRACHEAL INTUBATION SUPPORT INSTRUMENT

This application is a U.S. National Phase Application under 35 U.S.C. § 371 of International Patent Application No. PCT/JP2015/072556, filed Aug. 7, 2015, and claims the benefit of Japanese Patent Application No. 2014-161671, filed Aug. 7, 2014, all of which are incorporated by reference in their entirety herein. The International Application was published in Japanese on Feb. 11, 2016 as International Publication No. WO/2016/021724 under PCT Article 21(2).

FIELD OF THE INVENTION

The present invention relates to an endotracheal intubation support instrument by which an endotracheal tube for artificial ventilation is reliably inserted into a trachea of a patient having difficult airway which takes up much of cause of death under general anesthesia, especially, an endotracheal intubation support instrument which makes it easy to execute fiber-optic endotracheal intubation where a fiber-optic bronchoscope is used, the fiber-optic endotracheal intubation being executed for a patient having a high difficulty to execute endotracheal intubation.

BACKGROUND OF THE INVENTION

The endotracheal intubation treatment is sometimes required in medical practice for securing an airway of a patient having difficult airway. For example, the endotracheal intubation treatment is required in the following patients: a patient whose airway is blocked because of an accident or the like; a patient whose airway is impossible to be secured because of his/her coma state, drunkenness, or the like; a patient whose breathing has reduced or stopped because of anesthesia or the like; and a patient who needs the stent placement to his/her bronchus. The endotracheal intubation includes an oral intubation method where a tube is inserted from an oral cavity into a trachea and a nasal intubation method where a tube is inserted from a nasal cavity into a trachea.

In the conventional art of the endotracheal intubation, a stylet with a laryngoscope or a light guide is used, and for example, there is such a method that an operator introduces a tip of endotracheal tube from the inside of the laryngeal cavity to the glottis while checking visually, and then inserts the tip into the trachea.

Both of the oral intubation method and the nasal intubation method have a difficult point of endotracheal intubation. The difficult point is that it is hard to find the glottis which is an entrance of the trachea of the patient. A human body is structured in such a way that an esophagus and a trachea are diverged from each other at the vicinity of the larynx and pharynx. When the endotracheal tube is simply pushed into the trachea from the oral cavity, the endotracheal tube is generally inserted into the esophagus. The trachea is located on the chest side further than the esophagus is, and a diverging portion extending from the pharynx to the larynx is angled. The angle of the entrance of the trachea is different depending on each person. Further, the endotracheal tube has to go through various structures of a human body until reaching the trachea, such as the shape of the oral cavity, the state of the glossa, the shape of the larynx, the shape of the epiglottis, and the shape of the laryngeal cavity. Due to this, for example, in an emergency where it is necessary to secure the airway as early as possible, it is not easy to put an endotracheal tube through a trachea appropriately in short time.

As a measure for executing an endotracheal intubation most safely and reliably for a patient having a difficulty in the endotracheal intubation, there is known to be a measure of fiber-optic endotracheal intubation where an operator intubates to the trachea while seeing the area from the oral cavity to the trachea with a fiber-optic bronchoscope (hereinafter, referred to as the bronchial fiber).

The "bronchial fiber" is one kind of endoscopic instruments having 2 mm to 6 mm diameter. The bronchial fiber is inserted from the mouth or nose, introduced toward the glottis via the inside of the oral cavity or the inside of the nasal cavity while the image of the scope of the bronchial fiber is checked, and then inserted into the trachea; and thereafter, the endotracheal tube, which has been set in advance on a root portion of the fiber, is slid down by using the bronchial fiber as a guide, and inserted to and placed in the trachea (JP-A-2002-505925).

Further, as a conventional art, there is known to be a measure that, in consideration of the difficulty of the endotracheal intubation, wire is driven to the inside of the trachea from the a body surface side near the chest and drawn from an oral cavity side; and thereafter, the endotracheal tube is put into the wire to be inserted into the trachea by using the wire as a guide (JP-A-2003-235978). This measure disclosed in JP-A-2003-235978 is shown in FIGS. 20A and 20B.

Technical Problem

As mentioned above, the bronchial fiber functions as a guide for inserting the endotracheal tube into the trachea, and as a support of the endotracheal intubation. That is, since it is difficult for an operator to directly pass the endotracheal tube into the trachea while feeling his/her way to the trachea, first, the operator passes the bronchial fiber into the trachea from the oral cavity, and then inserts while sliding the endotracheal tube by using the bronchial fiber as a guide.

However, it is a problem that a manipulation for passing the bronchial fiber, which should be the guide, to into the trachea from the oral cavity is not easy.

First, in the bronchial fiber insertion process, there is such a problem that the visual field of the bronchial fiber is often interrupted. There are various kinds of obstacles on the way where the bronchial fiber reaches the trachea from the oral cavity. For example, the glossa, the saliva, the epiglottis and the like could be obstacles which interrupt the viewing field of the bronchial fiber. Especially, if a tracheal entrance is blocked by the epiglottis, it is not ease to view the trachea. The viewing field established by the bronchial fiber is narrow. Due to this, if some obstacles exist in the moving direction, it is difficult to grasp an entire image of the circumference, and thereby it is not easy to determine a felicitous avoidance-route.

Next, there is such a problem that the manipulation for the bronchial fiber requires a high skill. The bronchial fiber has a movable manipulation portion which is allowed to flex only in a vertical direction and a tube, the movable manipulation portion the length of which is approximately 2 centimeters being provided at the tip of the tube the length of which is approximately tens of centimeters, and the movable angle is up to 90 degrees. Further, the viewing angle of the scope is narrow, that is, between approximately 120 degrees and 130 degrees. Due to this, it is difficult to view a side field. In a case that the operator cannot view the tracheal entrance during the intubation process because of an obstacle, the operator is required to avoid the obstacle. However, it requires skill not obtained without sufficient manipulation experience to control the fiber to be introduced quickly to the trachea under such a condition that the movement and view field are restricted as mentioned above Further, much of an insertion portion of the bronchial fiber is configured as a flexible tube. Due to this, even if the operator tries to push away the obstacle blocking the front in order to progress the fiber, in many cases, the operator cannot move ahead the fiber sufficiently because of the flexibility of the fiber. Accordingly, even if the obstacle is small, the operator has to bypass the obstacle to move ahead the fiber. This would make the manipulation of the bronchial fiber more difficult.

There is a further problem which is a diversity of airway by an individually different structure, a deformation because of a prior medical operation, or the like, with respect to each of the oral cavity, the pharynx, the larynx, and the trachea. That is, in a case that the airway was deformed by a prior medical operation, or a portion around the airway suffered a big damage by an accident or the like, for example, the head and neck portion of the patient might be unmovable because the extensibility of his/her cervical portion has been lost by the damage of his/her cervical spine, it is impossible to move the head and neck portion side of the patient so that the bronchial fiber is easily operated. Due to this, the condition for manipulating the bronchial fiber becomes further difficult. In this way, the state of airway of the patient is diverse. This is one of causes which make manipulation of the bronchial fiber further difficult.

As mentioned above, the manipulation for inserting the bronchial fiber into the trachea via the larynx from the oral cavity is difficult and requires a very high skill.

With respect to the prior art, JP-A-2002-505925 discloses the measure for the lung after placing the endotracheal tube, for example, the measure for blocking the airway of one-lung and establishing the airway of the other one. However, this measure does not solve the difficulty of the endotracheal intubation itself.

The measure disclosed by JP-A-2003-235978 of the conventional art solves the difficulty of the endotracheal intubation itself. However, since it is required to drive thin wire with an injection into the airway from the body surface side, the invasiveness is high and the patient suffers a physical burden. Further, it is not easy to manipulate the wire driven to be introduced from the trachea up to the oral cavity via the glottis, the larynx, and the pharynx.

In light of the above problems, the present invention aims to provide an endotracheal intubation support instrument which is a support instrument such that even if an operator is not used to manipulating the bronchial fiber, the bronchial fiber is easily passed into from the oral cavity up to the trachea and the endotracheal tube is easily inserted into the trachea in a state that the epiglottis blocks the tracheal entrance.

SUMMARY OF THE INVENTION

Solution to Problem

In order to accomplish the above aim, an endotracheal intubation support instrument according to one aspect of the present invention is an endotracheal intubation support instrument for, prior to endotracheal intubation where an endotracheal tube is inserted from an oral cavity of a patient into a trachea, introducing and passing a bronchial fiber from the oral cavity into the trachea, comprising: a main body section having flexibility; a handle section and a blade section, each being provided in such a way as to extend from each end of the main body section; and a U-shaped groove being provided in such a way as to extend from the handle section to the blade section through the main body section, open from a central portion of a cross section of the U-shaped groove toward one side with respect to a short axial direction, and allow a flexible tube of the bronchial fiber to enter and get out of the U-shaped groove freely, wherein the blade section comprises a flap subsuming all or a part of a larynx of the patient and a lifting body having on both banks of the U-shaped groove, a first protruding portion heaving in a mountain shape and a second protruding portion being provided next to a main body section side of the first protruding portion and heaving in a mountain shape, the flap having walls smoothly extending toward a direction where the U-shaped opens from an end portion of a side surface of each side of the main body section, so that an outline of the blade section is in an almost concave shape, and when the U-shaped groove is located at a position facing the larynx of the patient, the first protruding portion being allowed to contact with a peripheral portion of an epiglottis of the patient, and the second protruding portion is allowed to contact with a peripheral portion of a glossal root of the patient.

Further, it is preferable to provide a bridge in an inside region of the flap, the bridge including chips extending from the banks of the U-shaped groove toward a center respectively, and working as a placing stand which a part of the bronchial fiber is placed on.

By the above configuration, according to the endotracheal intubation support instrument, even if the blade section is inserted into the oral cavity and just pushed, the tip portion of the blade moves ahead along a back wall of the pharynx. At this moment, flaps existing right and left sides of a forward portion of the blade catch a bump of the larynx. Due to this, the center of the blade is introduced along an axis connecting the trachea and the glottis. The epiglottis and the glossal root are raised by the first protruding portions and the second protruding portions each heaving in a mountain like shape at a backward position of the flap. Because of this, it is possible to establish an airway space by the U-shaped groove. In this state, if the bronchial fiber is inserted along the U-shaped groove from the oral cavity side, the bronchial fiber is introduced to a vicinity of the glottis portion without interruption by structures in the oral cavity and the pharynx cavity. Accordingly, the glottis can be easily viewed by image from a finder of the bronchial fiber. To "open from a central portion of a cross section of the U-shaped groove toward one side with respect to a short axial direction" means opening toward the front side of the endotracheal intubation support instrument of the present invention.

With respect to a configuration where the bridge is added, generally, the glottis exists above the bridge. Due to this, when the bronchial fiber is moved ahead from the U-shaped groove into the trachea, by manipulation to the fiber before reaching the bridge, a root of a movable manipulation portion of the fiber is raised because of the bridge above the U-shaped groove. That is, the bridge works as a placing stand. Thereby, since the bronchial fiber is allowed to easily turn for direction, it is possible to insert the fiber into the trachea quickly and reliably.

Further, in a case that the glottis exists in a moving direction of the U-shaped groove, it is possible to insert the fiber into the trachea by making the fiber go straight ahead with sliding under the bridge. In this case, because of the flexibility of the chips of the bridge, the blade is allowed to be removed easily from the fiber.

The main body section may be bent gently in a S-shape, the blade section may be provided in such a way as to extend from an end of a side where an opening surface of the U-shaped groove of the main body section curves inward, and the handle section may be provided in such a way as to extend from an end of a side where the opening surface of the U-shaped groove of the main body section curves outward. "A side where an opening surface of the U-shaped groove of the main body section curves inward" means one of sides of the main body section where the opening surface exists at an inside of the bent. "A side where the opening surface of the U-shaped groove of the main body section curves outward" means the other one of the sides of the main body section where the opening surface exists at an outside of the bent. This configuration is preferable, because the states of the endotracheal intubation support instrument at the moment of and after the insertion are easily fitted to the shapes from the oral cavity to the pharynx. Further, the curve of the handle section side makes it easy to support the handle and also makes the U-shaped groove exposed, in a state that the present endotracheal intubation support instrument is inserted. Therefore, there is such an effort that the present endotracheal intubation support instrument does not become encumbrance to the insertion manipulation of the fiber scope to be executed thereafter.

The flap may include wall boards which raise from the end portion of the side surface of each side of the main body section and extend widely toward a tip of insertion in a trapezoidal shape, so as to subsume the larynx, the main body section and an end of the flap may be made of a smoothly continuing thin plate in an almost concave shape viewed from a front, and a tip portion of the flap may gently curl outward. According to this configuration, at the moment of insertion of the present endotracheal intubation support instrument, even if there is a structure in the moving direction, the tip portion of the blade is allowed to enter a gap between the back wall of the pharynx and the structure to push the structure away. Further, the tip portion of the blade is formed in a trapezoidal shape widely, so that the blade looks like an almost concave wall. In other words, the blade extends so that a distance between flap walls gets larger gradually toward the tip of the insertion direction. Therefore, even if the endotracheal intubation support instrument goes off a center of a direction where the instrument should move ahead, it is possible to catch the larynx. Therefore, a positional relation between a center of the blade and a position of the glottis portion is converged so that their positions coincide with each other as the insertion progresses. The end of the flap is formed in an almost concave shape by using a thin plate. Because of this, at the end point of the insertion of the endotracheal intubation support instrument of the present invention, the tip of the flap easily fits the shapes of the hypopharynx and the piriform recess. As a result of that, since the U-shaped groove of the main body section is located stably along an axis from the trachea up to the glottis, it is possible to easily catch the glottis in the viewing field of the bronchial fiber.

The gap located at the vicinity of the central portion between the chips, arranged in a right-left direction, constituting the bridge may be provided obliquely to a center line of the U-shaped groove. According to this configuration, in a state that the endotracheal intubation support instrument of the present invention is inserted, even in a case that the flap is spread out because of the structure of an organ or the like, and thereby the chips constituting the bridge are opened in a right-left direction, that is, the gap is opens widely, the bridge is still capable of functioning as a placing stand where a part of the bronchial fiber is placed on. In other words, even if the gap is opened widely, the direction of the gap is oblique to the inserted bronchial fiber, thereby the bronchial fiber is difficult to pass through the gap and drop down to the U-shaped groove.

The lifting body may have an incision, the incision being: allowed to take in a tip of a peripheral portion of the epiglottis; and provided between the first protruding portion and the second protruding portion, wherein in a case the epiglottis blocks the trachea, by manipulation to the handle section to control a position of the blade section, the incision may be allowed to catch and raise the tip of the epiglottis to open the epiglottis for establishing a viewing field toward the trachea.

Here, distinctive points of incisions of the lifting body will be described.

The incision of the lifting body has a structure for raising the epiglottis which is blocking the tracheal entrance. Therefore, it is preferable to form multistage-structure using protruding portions in order to raise the epiglottis more reliably. Due to this, the structure for the incision of the lifting body comprises: a first protruding portion; a second protruding portion provided at a handle section side further than the first protruding portion; and an incision formed between the first protruding portion and the second protruding portion. With respect to a shape of each component, the following shape is preferable. The second protruding portion is formed in a protruding shape so as to contact with the peripheral portion of the glossal root, the incision has a shape for taking the peripheral portion of the epiglottis therein, and the first protruding portion is formed in a shape so as to contact with the surface of the peripheral portion of the epiglottis in a state the peripheral portion of the epiglottis is being taken in the incision.

According to the above configuration, even if the patient is in a state that the epiglottis is blocked, in a state that the flap stays at a vicinity of the tracheal entrance, the second protruding portion of the lifting body contacts with the peripheral portion of the glossal root and the first protruding portion contacts with the peripheral portion of the epiglottis blocking the larynx. Due to this, when the endotracheal intubation support instrument of the present invention inserted into the patient is slowly pulled back and moved upward, it is possible to raise the glossal root portion and the epiglottis. Thereby, since the tracheal entrance is opened, it becomes easy to find the glottis via the viewing field of the bronchial fiber. Further, since the tip of peripheral portion of the epiglottis is accepted by and engaged with the incision, it is possible to stably catch the periphery of the epiglottis. Thereby, since the epiglottis is possible to be raised reliably so that the glottis is visualized, it is possible to secure the viewing field toward the trachea.

Here, it is preferable that the second protruding portion of the lifting body is higher than the first protruding portion. Because this configuration is in consideration of the shape of the peripheral portion of the epiglottis and the shape of the peripheral portion of the glossal root, a balance becomes better.

The present endotracheal intubation support instrument may include a suction passage sucking body fluid and the like and having a first end opening in the flap of the blade section and a second end opening at the handle section, so that the suction passage runs through the flap, the main body section, and the handle section. In this case, in a case that the bronchial fiber is being inserted into the body, it is possible to remove body fluid including saliva and blood which could be an obstacle against the viewing field of a finder, water vapor causing fog, and the like. Accordingly, for the manipulation of the bronchial fiber, it is possible to maintain a good view.

Further, in order to make the suction passage detachable and attachable, instead of the suction passage built-in, an engagement groove may be provided for engaging with the suction tube. In a case that the present endotracheal intubation support instrument is used repeatedly, since the suction tube is changeable, the repeated use in a sanitary state is preferable.

Next, as a distinctive point for introducing the manipulation of the bronchial fiber with using the endotracheal intubation support instrument of the present invention, it is preferable that coloring or mark as a guide is provided on either the blade section or the main body section. In the process of insertion of the bronchial fiber, because of limitation of the viewing field of the scope, it is difficult to specify precisely the tip position of the fiber by the image. However, if a coloring or a mark is provided as a position guide in the moving direction of the U-shaped groove, it is possible to easily recognize the tip position by the coloring or the mark displayed in the image. Therefore, it is possible to easily view a state that the tip position of the bronchial fiber has closed to or reached the vicinity of the bridge of the blade section from a position before the entrance of the airway.

Next, distinctive points of the U-shaped groove of the main body section will be described.

First, the width of the U-shaped groove is preferably a little larger than a diameter of the bronchial fiber. If the width of the U-shaped groove is a little larger than the diameter of the bronchial fiber, in a case that the flexible tube portion of the bronchial fiber housed in the U-shaped groove of the main body section is introduced to the tracheal entrance together with the main body section, it is possible to easily remove the bronchial fiber from the U-shaped groove and make only the bronchial fiber enter the trachea. On the other hand, in a case of unnecessary, it is possible to easily pull out the present endotracheal intubation support instrument.

Next, it is preferable that fine roughness like ground-glass or at least one fine rib, a top of each rib being sharp, is provided on a surface of the U-shaped groove, in order to reduce friction resistance produced by contact of the bronchial fiber and the U-shaped groove. Thereby, the bronchial fiber moves easily in the U-shaped groove.

Next, with respect to a length of the endotracheal intubation support instrument of the present invention and a shape of the handle section, distinctive points will be described.

The present endotracheal intubation support instrument may be configured such that a length and a shape of the endotracheal intubation support instrument are adjusted so that a back end of the handle section is located at a vicinity of outside of the oral cavity of the patient and also an oxygen mask is allowed to put on the patient, in a state a tip of the blade section is located at a vicinity of the epiglottis of the patient. As the shape of the handle section, it is preferable that a thickness gets thinner from the main body section toward the handle section, and a thin portion is designed in such a way as to be easily bent and curled.

According to the above distinctive points with respect to the length of the endotracheal intubation support instrument and the shape of the handle section, it is possible to supply, prior to the insertion of the bronchial fiber, oxygen sufficiently to the patient so that the patient is oxygenated by the artificial ventilation, thereby time when the patient can bear with apnea is considerably extended. Due to this, it is possible to prevent hypoxemia caused by apnea of the patient during a series of intubation manipulation. Accordingly, safety of the intubation manipulation itself is enhanced. That is, after the present endotracheal intubation support instrument is inserted to the patient and the airway is established, a face mask is put on the patient so that the handle section protruding from the mouth is housed within the face mask. Thereafter, oxygen is supplied via the face mask to oxygenate sufficiently the inside of the body. After that, the mask is put off and suction is executed as necessary. And then, the bronchial fiber to which the endotracheal tube has been set in advance is inserted into the trachea along the U-shaped groove. At the moment of insertion of the bronchial fiber, if necessary, the position of the present endotracheal intubation support instrument should be adjusted. After the bronchial fiber is inserted into the trachea, the present endotracheal intubation support instrument is pulled out, and the trachea tube is inserted into the trachea along the bronchial fiber. And then, in a state that the endotracheal tube is placed, the bronchial fiber is pulled out. It is possible to execute such a series of manipulations while preventing the hypoxemia of the patient.

If the handle section is designed in an elliptically spread shape like a rice scoop for helping grasp, and has a groove for fold on a back surface of the handle section, positional adjustment and pullout manipulation to be executed after the insertion of the present endotracheal intubation support instrument become easy. In addition, since the handle section is allowed to be folded along the grooves provided on the back surface thereof, it becomes easy to house the handle section within the face mask.

The endotracheal intubation support instrument of the present invention mentioned above is also specified by the following constructions. That is, an endotracheal intubation support instrument which is, prior to endotracheal intubation where an endotracheal tube is inserted from an oral cavity of a patient into a trachea, inserted to the oral cavity of the patient, the endotracheal intubation support instrument comprising: a main body section having flexibility; a blade section being provided at a forward end of the main body section in an insertion direction; a handle section being provided at a backward end of the main body section in the insertion direction; and a U-shaped groove being provided in such a way as to extend from the handle section up to the blade section through the main body section, and open toward a front side of each of the main body section, the blade section, and the handle section, wherein the blade section comprises: a flap having a pair of side walls extending spacedly from both end portions with respect to a traverse (transverse) direction of the U-shaped groove toward the front side; and a lifting body being arranged at a position sandwiched by the pair of the side walls of the flap, and having a first protruding portion and a second protruding portion next to a backward portion of the first protruding portion in the insertion direction provided on each of both sides with respect to the traverse direction of the U-shaped groove.

By using the above endotracheal intubation support instrument, it becomes easy to find the glottis by the bronchial fiber, and it becomes easy to insert the bronchial fiber into the trachea.

Especially, even if the epiglottis blocks the tracheal entrance, by insertion from the oral cavity, the endotracheal intubation support instrument is engaged with a predetermined position of the hypopharynx, the first protruding portion and the second protruding portion of the lifting body are located in such a way as to face the peripheral portion of the epiglottis and the peripheral portion of the glossal root respectively. Accordingly, by the operation of the lifting body, it is possible to raise the epiglottis while raising the peripheral portion of the glossal root.

Thereby, since the tracheal entrance can be opened by raising the epiglottis with raising the glossal root by using the lifting body, if the glottis can be viewed, it is easily possible to make the bronchial fiber move ahead into the trachea.

As one of embodiments of the endotracheal intubation support instrument, the above endotracheal intubation support instrument may further comprise a bridge arranged at a position sandwiched by the pair of side walls of the flap and provided in such a way as to traverse above the U-shaped groove, wherein the bridge has a pair of chips extending from both sides with respect to the traverse direction of the U-shaped groove respectively and facing each other above the U-shaped groove, and a gap is formed at a position where the pair of chips faces each other. In this embodiment, the gap may be provided obliquely to a center line of the U-shaped groove. Further, as the other embodiment of the endotracheal intubation support instrument of the present invention, the flap may be designed so that a space between the pair of side walls expands gradually toward a forward portion of the flap in the insertion direction. Further, a penetrating hole penetrating the handle section may be formed in the handle section. In this case, when an oxygen mask is put on the patient to whom the endotracheal intubation support instrument is inserted, even if the handle section is located at a position where the vent of the oxygen mask is blocked, it is possible to secure breathability by the penetrating hole formed in the handle section. That is, it is possible to prevent the vent of the oxygen mask from being blocked by the handle section. With respect to the penetrating hole, the position, size, and number of pieces are allowed to be varied as appropriate.

BRIEF DESCRIPTION OF THE DRAWINGS

FIG. 2 is a rear perspective view of the endotracheal intubation support instrument according to the present invention.

FIG. 5A is a longitudinal sectional view taken along line A-A of FIG. 3A.

FIG. 8A is a first diagram which simply shows a state that a bridge is used as a lift stand which a vicinity of a tip of a bronchial fiber is placed on;

FIG. 8B is a second diagram which simply shows a state that the bridge is used as the lift stand which the vicinity of the tip of the bronchial fiber is placed on.

FIG. 8C is a third diagram which simply shows a state that the bridge is used as the lift stand which the vicinity of the tip of the bronchial fiber is placed on.

FIG. 9A is a first diagram which simply shows procedure that the tip of the bronchial fiber is made to pass under the bridge and move ahead, and thereafter, the endotracheal intubation support instrument of the present invention is pulled out.

FIG. 9B is a second diagram which simply shows procedure that the tip of the bronchial fiber is made to pass under the bridge and move ahead, and thereafter, the endotracheal intubation support instrument of the present invention is pulled out.

FIG. 20A is a diagram using FIG. 1 shown in JP-A-2003-235978 to explain procedure of retrograde endotracheal intubation.

DETAILED DESCRIPTION OF THE INVENTION

Hereinafter, in reference to drawings, an embodiment of an endotracheal intubation support instrument as one aspect of the present invention will be described. However, the technical scope of the present invention should not be limited to the specified purpose, shape, size, quantity, and the like shown in the following embodiment.

Hereinafter, the endotracheal intubation support instrument of the present invention is sometimes abbreviated to "the present endotracheal intubation support instrument".

Further, in the expression "the surface of a peripheral portion of the epiglottis" being used in the description, this "surface" indicates a surface on a side facing the glottis.

A configuration example of an endotracheal intubation support instrument 100 according to the present invention will be shown.

Figure 1:
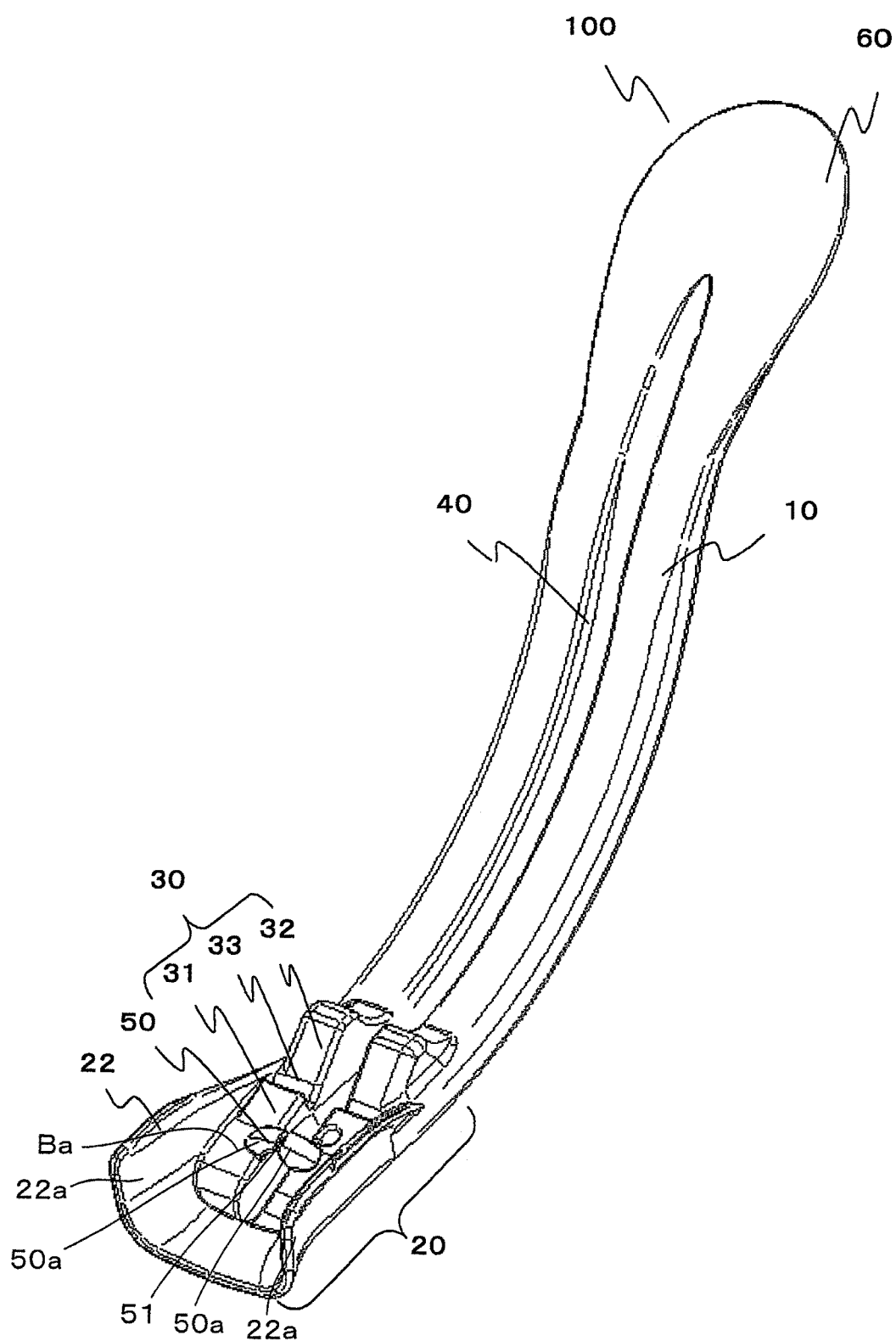
FIG. 1 is a front perspective view of an endotracheal intubation support instrument according to the present invention.

FIG. 1 is a front perspective view showing a configuration example of the endotracheal intubation support instrument 100 according to the present invention.

FIG. 2 is a rear perspective view showing the configuration example of the endotracheal intubation support instrument 100 according to the present invention.

Figure 3A:
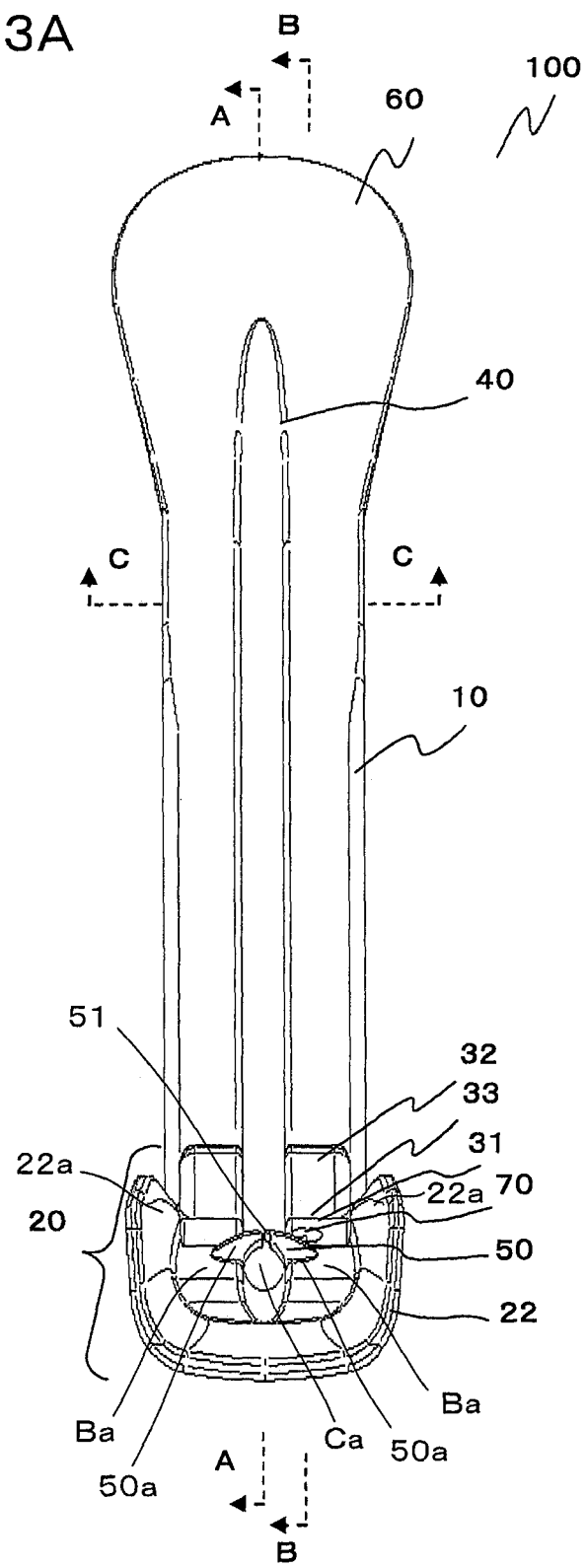
FIG. 3A is a front view of the endotracheal intubation support instrument according to the present invention.
Figure 3B:
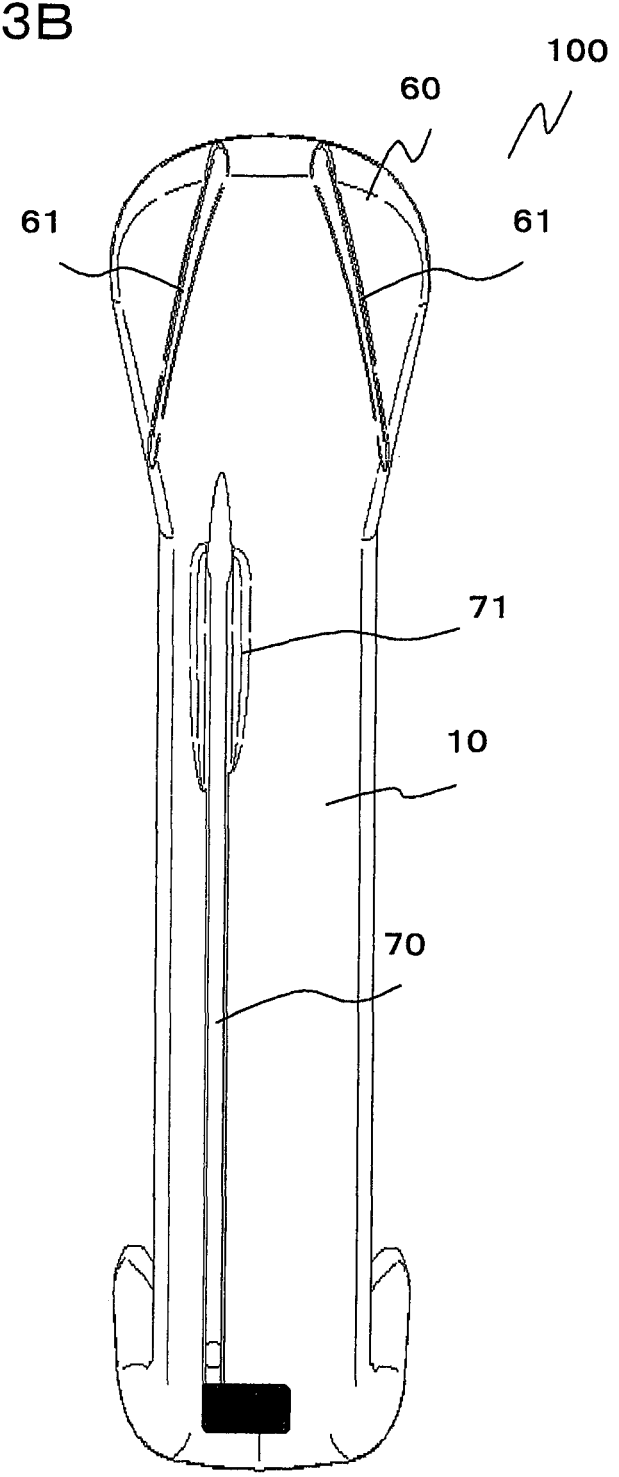
FIG. 3B is a rear view of the endotracheal intubation support instrument according to the present invention.

FIGS. 3A and 3B are front and rear views of the endotracheal intubation support instrument 100 according to the present invention respectively.

Figure 4A:
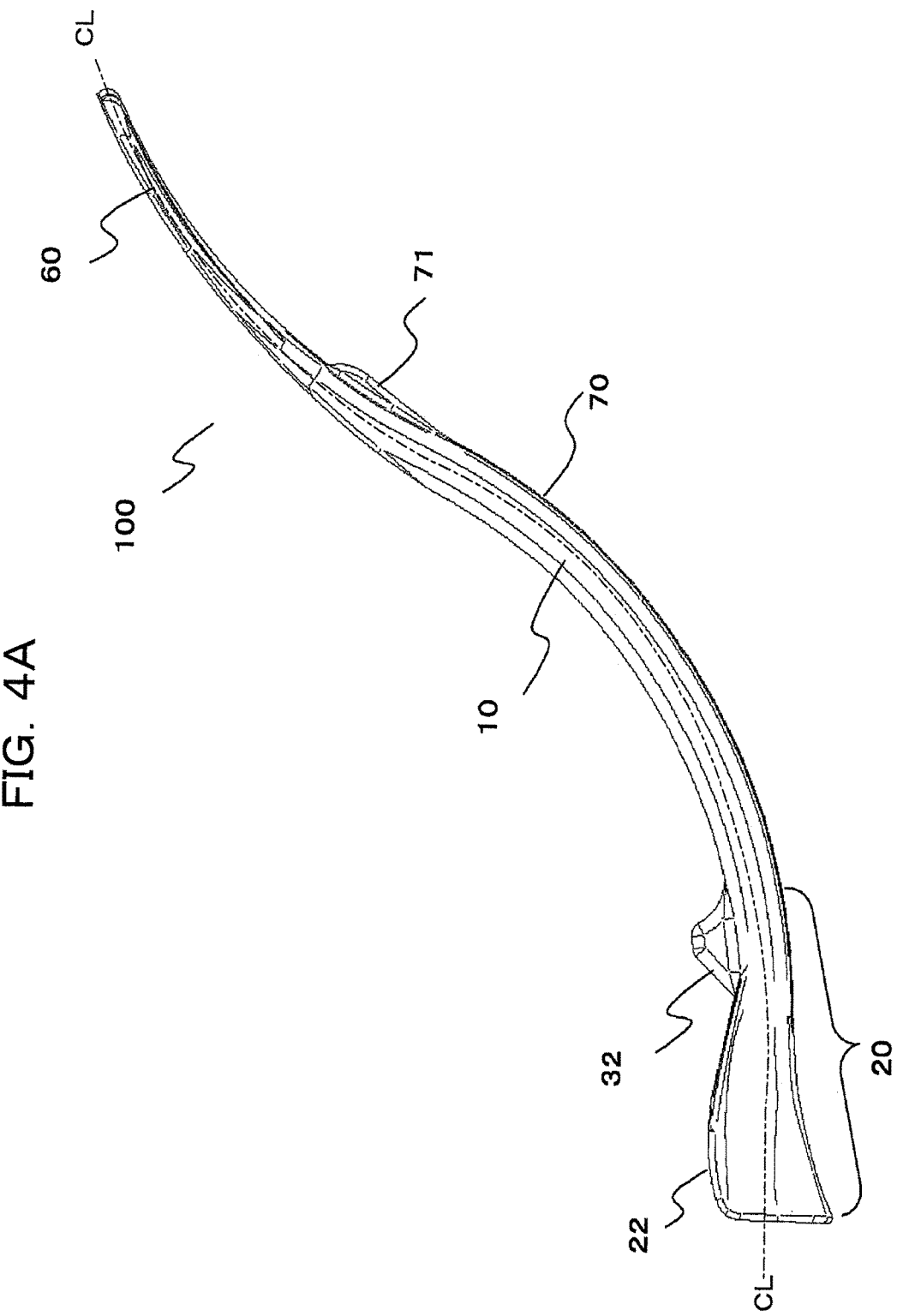
FIG. 4A is a left-side view of the endotracheal intubation support instrument according to the present invention.
Figure 4B:
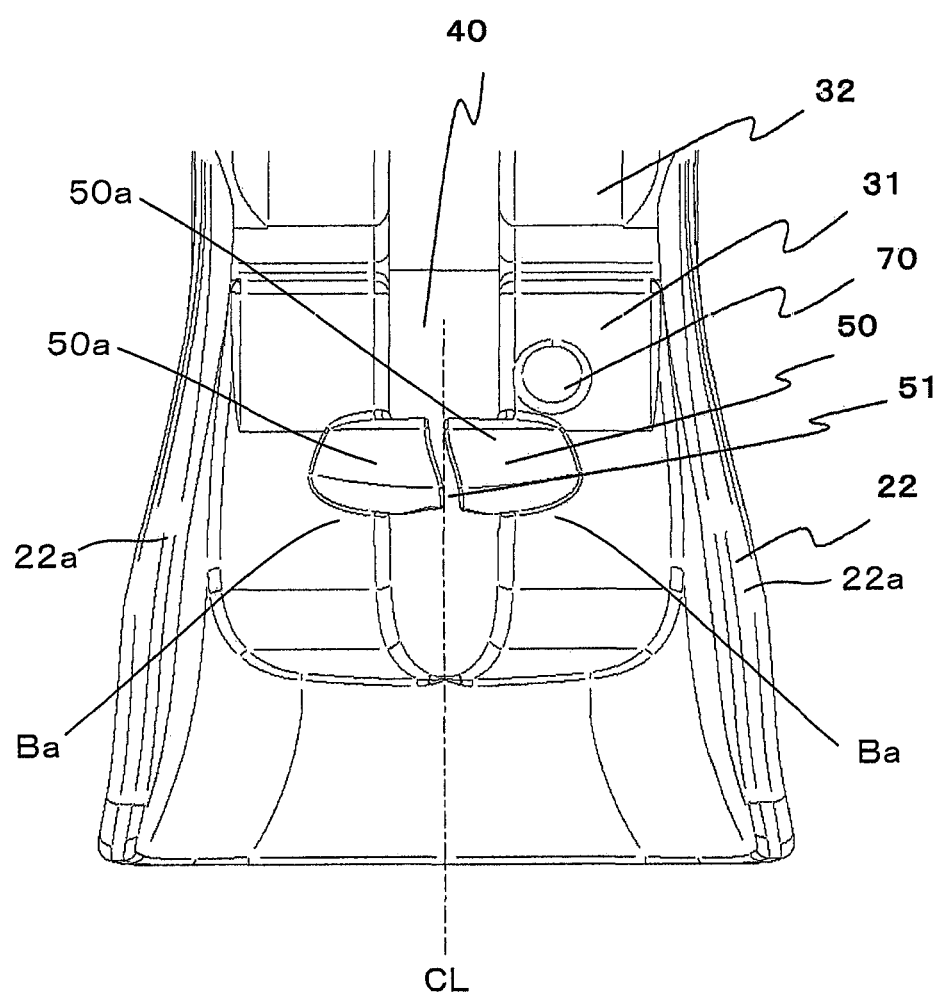
FIG. 4B is an enlarged plan view of a vicinity of a blade section.

FIG. 4A is a left-side view of the endotracheal intubation support instrument 100 according to the present invention, and FIG. 4B is an enlarged plan view of a vicinity of a blade section 20.

Figure 5B:
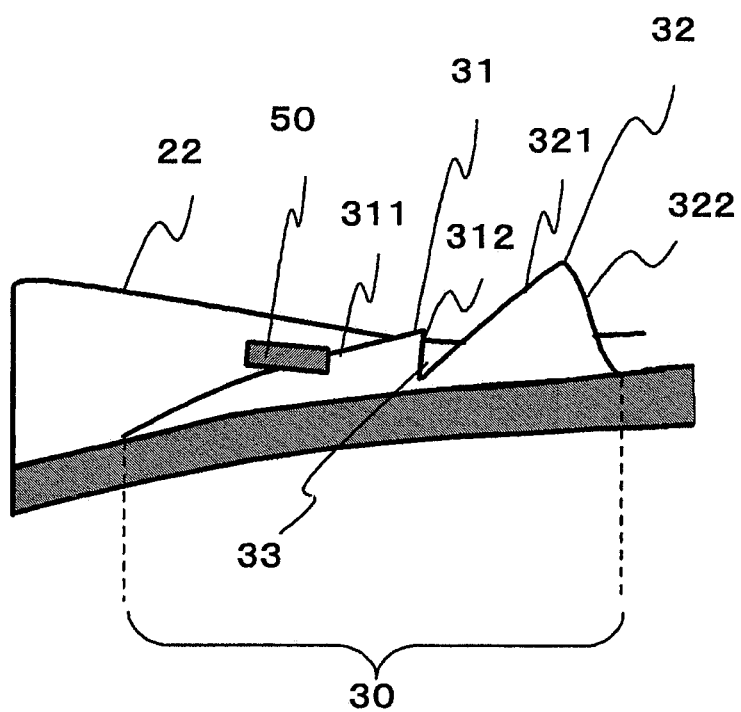
FIG. 5B is an enlarged diagram of the blade section and a lifting body.

FIG. 5A is a longitudinal sectional view taken along line A-A of FIG. 3A. FIG. 5B is an enlarged diagram of the blade section and lifting body in FIG. 5A.

Figure 6A:
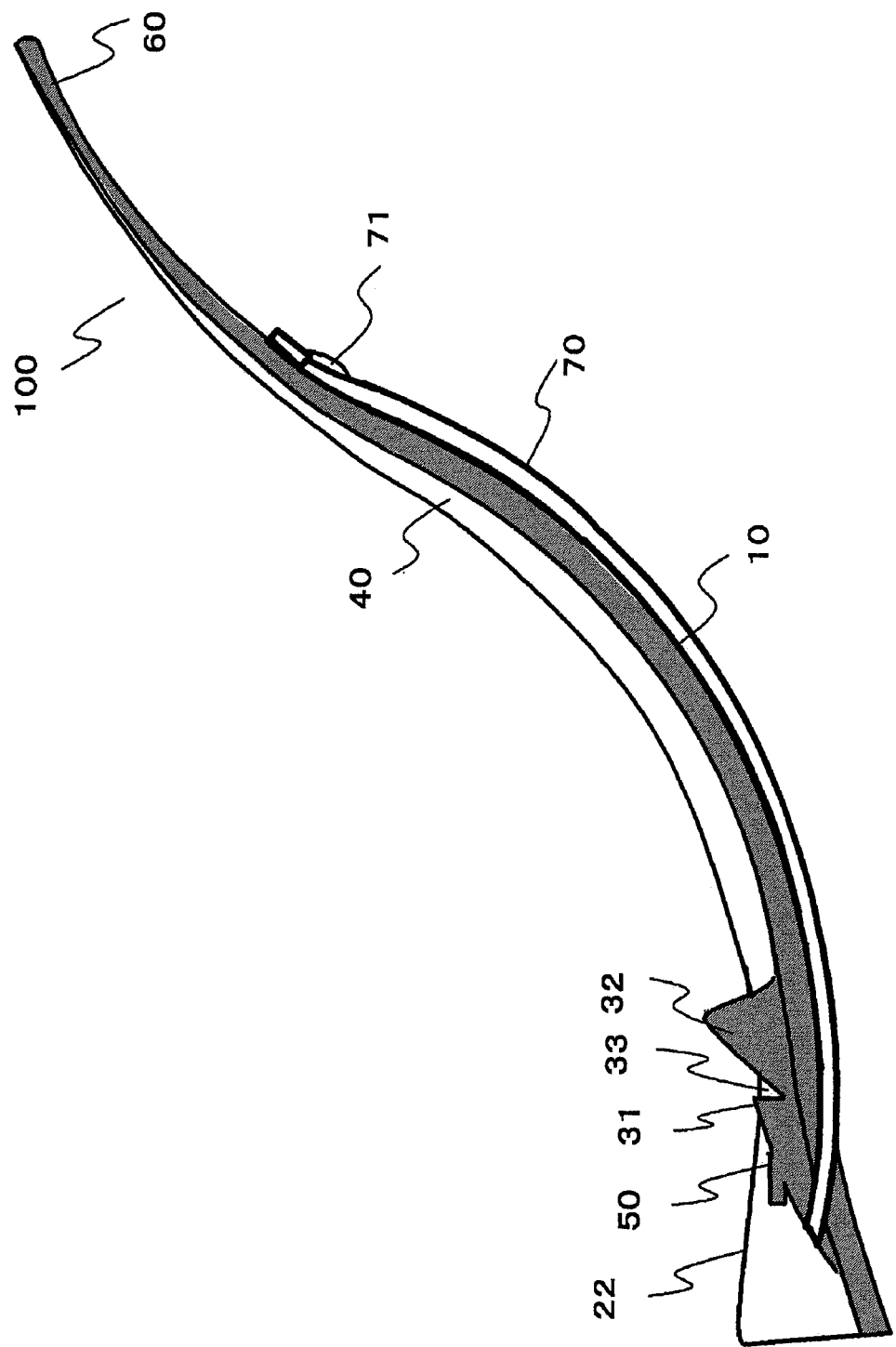
FIG. 6A is a longitudinal sectional view taken along line B-B of FIG. 3A.
Figure 6B:
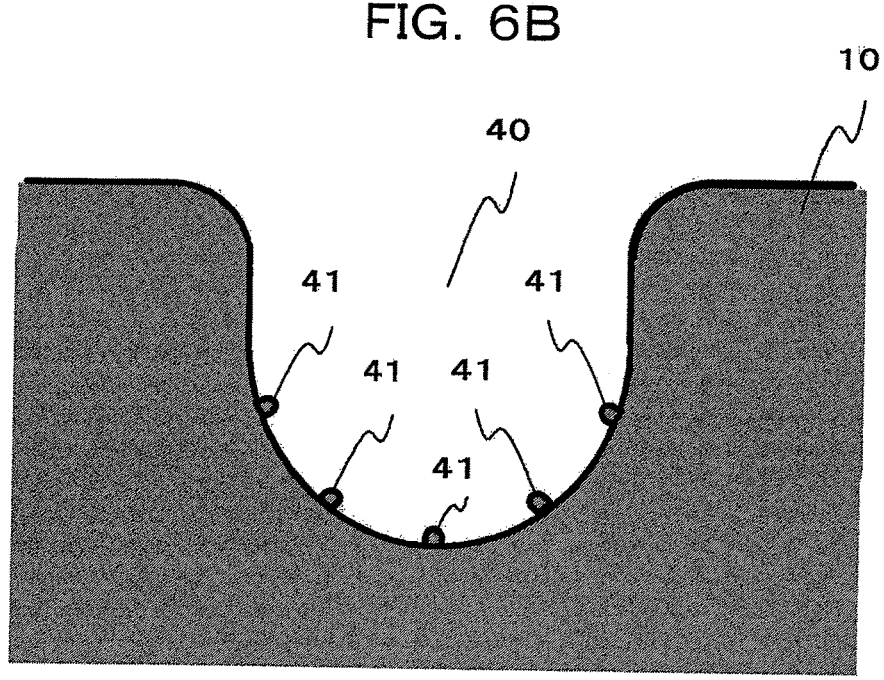
FIG. 6B is an enlarged diagram showing only a U-shaped groove extracted from a longitudinal section taken along line C-C of FIG. 3A.

FIG. 6A is a diagram for explaining a state that a suction tube is attached in a longitudinal sectional view taken along line B-B of FIG. 3A. FIG. 6B is an enlarged diagram showing only a U-shaped groove in a longitudinal sectional view taken along line C-C of FIG. 3A.

As shown in FIG. 1, the present endotracheal intubation support instrument 100 comprises: a main body section 10; the blade section 20; the lifting body 30; a U-shaped groove 40; a bridge 50; and a handle section 60.

Whole of the instrument 100, especially the main body section 10 and blade section 20, is made of material having flexibility and appropriate strength. For example, the instrument 100 may be obtained by curving a thick board made of silicon. The material should have flexibility in order to fit its insertion portion easily to a shape of an airway of a patient, the airway extending from the oral cavity up to the pharynx and larynx, and suppress damage against patient tissue as much as possible. Further, the material should have appropriate strength, because if the material does not have appropriate strength, when an operator inserts the main body section from the oral cavity to the pharynx and larynx, it would be impossible to make the main body section move ahead by a pushing manipulation from the operator side to make the main body section pass through between tissues blocking the direction of its movement. The material of the present endotracheal intubation support instrument 100 is not limited to silicon. The material may be vinyl chloride, polyurethane, foamed polyethylene, or the like which has the flexibility and appropriate strength.

The whole of the present endotracheal intubation support instrument 100 has a gently curved shape. The curved shape in the present configuration example is an S-shaped curve. The blade section 20 and the main body section 10 are provided for making it easy to insert the instrument 100 from the oral cavity to the pharynx, larynx, and a vicinity of an esophageal entrance, and for making it easy to fit their shapes after their insertion. Due to this, whole of the sections 20 and 10 has a gently curved shape, for example, having an S-shaped curve.

It is preferable that edges and the like of the present endotracheal intubation support instrument 100 are made gently round. The main body section 10 would contact with the patient tissue. The gently rounded shape could reduce damage against the patient tissue. Also, with respect to the blade section 20 located at a tip of the present endotracheal intubation support instrument 100, it is preferable that edges thereof are made gently round.

The blade section 20 is provided at a forward portion further than the main body section 10, and the handle section 60 is provided on an operator side further than the main body section 10. That is, with respect to the main body section 10, a direction toward a side where an opening surface of the U-shaped groove 40 curves inward is a tip direction. At an end of the main body section 10 with respect to the tip direction, the blade section 20 extends. A direction toward a side where the opening surface of the U-shaped groove 40 curves outward is a back-end direction with respect to the main body section 10. At an end of the main body section 10 with respect to the back-end direction, the handle section 60 extends. The present endotracheal intubation support instrument 100 is structured in this way. The side where the opening surface of the U-shaped groove 40 curves inward means one side of the main body section 10 where the opening surface exists on an inner side of the curve. The side where the opening surface of the U-shaped groove 40 curves outward means the other side of the main body section 10 where the opening surface exists on an outer side of the curve.

Next, the U-shaped groove 40 will be described.

The U-shaped groove 40 is a groove running from the handle section 60 through the main body section 10, and extending to the blade section 20. The groove 40 opens from a central portion of its cross-section toward one side with respect to a short axial direction. In other words, the U-shaped groove 40 is a groove which passes the main body section 10 from the handle section 60 and runs the blade section 20, the groove 40 opening toward the front side of the present endotracheal intubation support instrument 100. As shown in FIGS. 1 to 5B, a flexible tube of a bronchial fiber (not illustrated) where an endotracheal tube (not illustrated) is set is allowed to go in and out freely. That is, the U-shaped groove 40 functions as a guide for insertion of the bronchial fiber from the oral cavity up to the tracheal entrance, if the present endotracheal intubation support instrument 100 has been inserted to the airway of the patient in advance.

It is preferable that the width and depth of the U-shaped groove 40 are larger than an outer diameter of the bronchial fiber. The U-shaped groove 40 is a portion where the flexible tube of the bronchial fiber is temporally housed at the moment when the bronchial fiber is moved from the oral cavity toward the tracheal entrance. Due to this, the width and depth of the U-shaped groove 40 are required to house the flexible tube in a good condition. Further, as mentioned later, after the tip of the bronchial fiber reaches the tracheal entrance, only the bronchial fiber is inserted into the trachea. Because of this, the flexible tube of the bronchial fiber is required to leave easily from the U-shaped groove 40. Accordingly, since the outer diameter of the bronchial fiber is less than 6 mm in general, for example, the width of the U-shaped groove 40 may be 6 mm, and the depth of the groove 40 may be equal to or more than 6 mm.

In the above descriptions, one of configuration examples of the U-shaped groove is shown. It is possible to set the width and depth of the U-shaped groove arbitrarily. Further, it is also possible to set the groove in a concave shape, an omega shape, or the like arbitrarily.

The bronchial fiber is required to pass the glossal root and epiglottis being elevated by the lifting body 30, and reach the entrance of the airway. Because of this, with respect to the range of the U-shaped groove 40, a continuing groove is formed from the main body section up to the tip side further than the lifting body 30. In the present embodiment, as shown in FIG. 1, the U-shaped groove 40 extends up to the tip side much further than the bridge 50 located at the tip side further than the lifting body 30.

In the present endotracheal intubation support instrument 100, it is preferable that a part of the blade section 20 or a part of the main body section 10 is colored or marked. In the process of insertion of the bronchial fiber, if using the color or the mark as a lead, an operator can view a state that the tip position of the bronchial fiber reaches a vicinity of the bridge 50 of the blade section 20. In a case that the present endotracheal intubation support instrument 100 is made of half-translucent material, for example, if a region covering the U-shaped groove 40 on the rear surface of the blade section shown in FIGS. 2 and 3B is colored with blue or green, which is a complementary color of mucosal tissue, it is possible to confirm the tip position by the image of the bronchial fiber showing a state of passing through the U-shaped groove 40. The color, shape and position of the coloration are not limited to this configuration example, as long as the operator is allowed to confirm that the tip of the bronchial fiber reaches the vicinity of the bridge 50 of the blade section 20. For example, the inside of the U-shaped groove 40 may be colored. Or, the main body section 10 may be marked instead of the blade section 20 is.

Next, the following will describe a distinctive structure for friction reduction with respect to an inner wall surface of the U-shaped groove 40. When the bronchial fiber is inserted, since the inner wall surface of the U-shaped groove 40 contacts with the flexible tube, thereby friction resistance occurs. Due to this, it sometimes becomes difficult to move the bronchial fiber. Then, in order to reduce the friction coefficient, on the inner wall surface of the U-shaped groove 40, fine roughness (not illustrated) like ground-glass is provided, or, as shown in FIG. 6B, one or plural fine ribs 41 are provided. The fine roughness like ground-glass makes a contact area small, and thereby so-called "slippage" gets better. In the same way, the fine ribs make a contact area small and thereby so-called "slippage" gets better. Here, it is possible to determine arbitrarily whether the fine roughness or the fine ribs are provided or not.

Next, the following will describe the blade section 20.

As shown in FIGS. 1 to 4B, the blade section 20 comprises a flap 22, and is formed in a trapezoidal shape which is widen toward the tip. The flap 22 extends smoothly in an almost concave-shape and bisymmetrically from the end portion of each of the side surfaces of the main body section 10 toward a direction where the U-shaped groove 40 is opened. In other words, the flap 22 is designed so that the width thereof gradually gets larger toward the tip with respect to the insertion direction of the present endotracheal intubation support instrument 100. The tip portion of the blade section 20 is formed in a plate like shape so that the blade section 20 is easily inserted to the oral cavity and the pharynx, and edges thereof are provided with smoothly rounded. Since the blade section 20 touches mucosal tissue of a patient to make the portion spread out or to elevate the portion, if the edges are provided with smoothly rounded, it is possible to reduce damage against tissue of the patient.

As shown in FIGS. 1 to 4B, in this configuration example, in a region where the blade section 20 is provided, the flap 22, the lifting body 30, and the bridge 50 are also provided.

The flap 22 is, as shown in FIGS. 1 to 4B, formed in a shape that all or a part of the larynx of the patient is subsumed in a state that the flap is inserted into the trachea of the patient. The flap 22 is made of a smoothly extending thin plate where its tip is formed in an almost concave shape. The tip portion of the flap 22 is formed so as to fit easily the shapes of the esophagus and hypopharynx (including the piriform recess) in an insertion state. Further, the side walls 22a of the flap 22 are formed in a trapezoidal shape which is widen toward the tip. In other words, each of the pair of side walls 22a extends so that the width of the flap 22, that is, the space between the pair of side walls 22a gradually gets larger toward the tip with respect to the insertion direction. Due to this, even if the operator just inserts the present endotracheal intubation support instrument 100, since the inner wall of the flap 22 of the blade section 20 catches a wall surface of the larynx, the posture of the present endotracheal intubation support instrument 100 is naturally made to approach the center. Thereby, a positional relation between the present endotracheal intubation support instrument 100 and the trachea are corrected so that the center line of the present endotracheal intubation support instrument 100 is aligned with the center line of the trachea.

The tip portion of the flap 22 is smoothly and outwardly curled. Due to this, even if there is an obstacle in a direction of movement, the operator can make the tip portion of the flap 22 insert between a posterior wall of the pharynx and the obstacle, and move the flap 22 forward while pushing away the obstacle. Accordingly, at the end point of the insertion, the tip of the flap 22 easily fits the shape including the piriform recess from the hypopharynx up to the entrance portion of the esophagus. Further, since both of the side walls of the flap 22 support the constructions such as the oral cavity and the pharynx, it is possible to secure a moving area of the bronchial fiber of the U-shaped groove 40.

Next, the following will describe the lifting body 30.

As shown in FIG. 1, the lifting body 30 is a member standing sharply from the front of the blade section 20, and provided at a position which faces the epiglottis of the patient when the blade section 20 is inserted into the larynx of the patient.

The lifting body 30 comprises a first protruding portion 31 and a second protruding portion 32. The first protruding portion 31 is allowed to contact with a surface (a facing surface on the glottis side) of a peripheral portion of the epiglottis (a peripheral portion on the esophagus side of the epiglottis), and the second protruding portion 32 is allowed to contact with the surface of a peripheral portion of the glossal root. In this configuration example, as shown in FIG. 5B, each protruding portion 31, 32 comprises "an inclined portion" 311, 321 and "a hooking portion" 312, 322 which form, a triangle a vertex of which faces upward, in a vertical section of each of the protruding portions 31,32.

The inclined portion 311 of the first protruding portion 31 is provided in such a way as to gradually get higher toward the back-end side from the tip side of the blade section 20. When the blade section 20 passes down over the peripheral portion of the epiglottis, the inclined portion 311 contacts with the epiglottis and both of them slide each other. Thereby, the epiglottis does not interrupt the moving of the blade section 20. On the other hand, the hooking portion 312 of the first protruding portion 31 is cut back so that the vertex of the hooking portion 312 is formed as an angular protrusion. Thereby, if the blade section 20 is pulled back, the hooking portion 312 contacts with and hooks the surface of the peripheral portion of the epiglottis. Due to this, after the hooking portion 312 of the first protruding portion 31 catches the peripheral portion of the epiglottis, if the blade section 20 is pulled back, the epiglottis is allowed to be raised.

As mentioned above, the lifting body 30 has a feature in its arrangement position in the blade section 20, that is, the lifting body 30 is provided in such a way as to come to a position facing the epiglottis of the patient at a deeper side of the pharynx.

With respect to the lifting body 30, one example of the arrangement position and size will be described.

Preferably, the lifting body 30 is located at a position in the blade section 20 within a range between, for example, 10 mm and 50 mm from the tip of the blade section 20 as a start point. Because, since the lifting body 30 is a member for hooking and raising the epiglottis, it is preferable that the lifting body 30 is located near the epiglottis in a state that the tip of the blade section 20 is located at the esophageal entrance.

The height of the lifting body 30 is preferably about between 10 mm to 25 mm. Since the lifting body 30 is a member for hooking the epiglottis, some degree of size is required. However, if the size is too big, the size would cause interruption against the insertion to the oral cavity. Therefore, the above mentioned size is preferable.

Further, with respect to the width of the lifting body 30, about between 20 mm to 40 mm including the width of the U-shaped groove 40 is preferable. Of course, the size and arrangement position of the lifting body is not limited to one configuration example above mentioned, and it is possible to set arbitrarily the size and arrangement position.

Next, multistage-structuration of each of the protruding portions of the lifting body 30 will be described.

In the present configuration example, the protruding portion of the lifting body 30 is multistage-structured. The lift body should have a structure for raising the epiglottis blocking the trachea. If the protruding portion is multistage-structured, the epiglottis can be raised more reliably.

The lifting body 30 comprises the first protruding portions 31, the second protruding portions 32, and incisions 33 each being provided between the first protruding portions 31 and the second protruding portion 32.

The first protruding portions 31 are provided near the bridge 50 on banks Ba and Ba located at the blade section 20 side portion of the U-shaped groove 40 respectively. The first protruding portions 31 are formed in such a way as to heave symmetrically in a mountain shape to face the epiglottis of the patient, and each has the inclined portion 311 and the hooking portion 312. The first protruding portion 31 is formed in such a way as to be allowed to contact with the peripheral portion of the epiglottis, and allowed to raise the epiglottis when the handle section 60 is pulled up.

Each of the second protruding portions 32 is provided next to the main body section 10 side of the first protruding portion 31, and formed in such a way as to heave in a mountain shape. The second protruding portion 32 comprises the inclined portion 321 and the hooking portion 322. The second protruding portion 32 is formed in such a way as to be allowed to contact with the peripheral portion of the glossal root, and allowed to raise the glossal root when the handle section 60 is pulled up. By raising the glossal root when raising the epiglottis, it becomes easy to raise the epiglottis.

Further, in consideration of a difference between the sizes of the epiglottis and the glossal root, the balance is better when the height of the second protruding portions 32 is set to be higher than the height of the first protruding portions 31.

The incision 33 is a recess provided between the first protruding portion 31 and the second protruding portion 32. The size and depth of the incision 33 are determined so that the incision 33 is allowed to take in a tip of the peripheral portion of the epiglottis. If the tip of the epiglottis is accepted to and engaged with the incision 33, it is possible to catch stably the periphery of the epiglottis. Thereby, since it is possible to raise the epiglottis reliably to visualize a tracheal entrance portion, it becomes possible to secure a visual field toward the trachea.

In the above description, one of configuration examples with respect to the multistage-structuration of the protrusions of the lifting body was described. However, the number of the protruding portions or the incisions is not limited to this configuration example, and is allowed to increase arbitrarily.

Figure 7A:
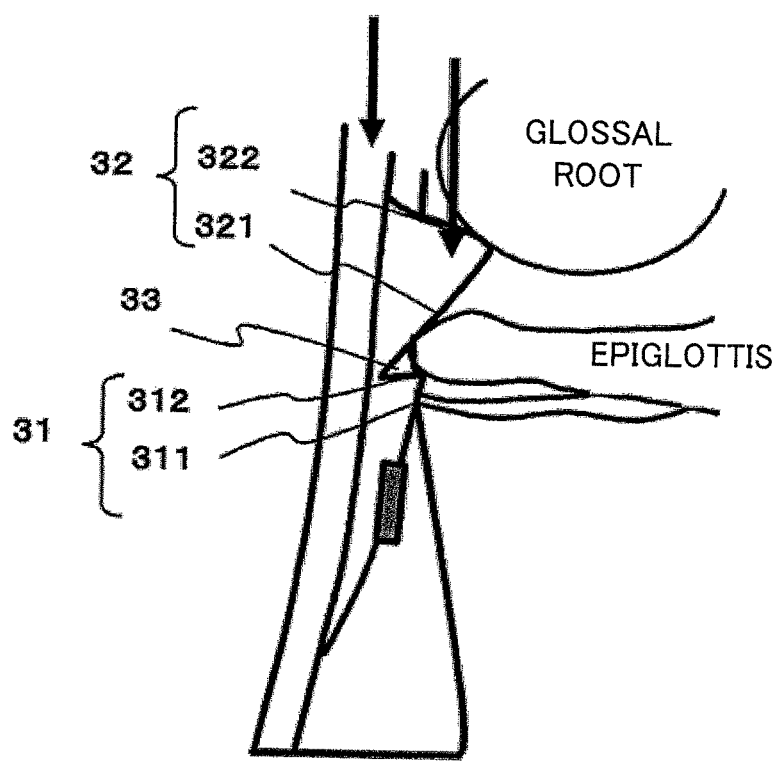
FIG. 7A is a first diagram showing an operation of the lifting body.
Figure 7B:
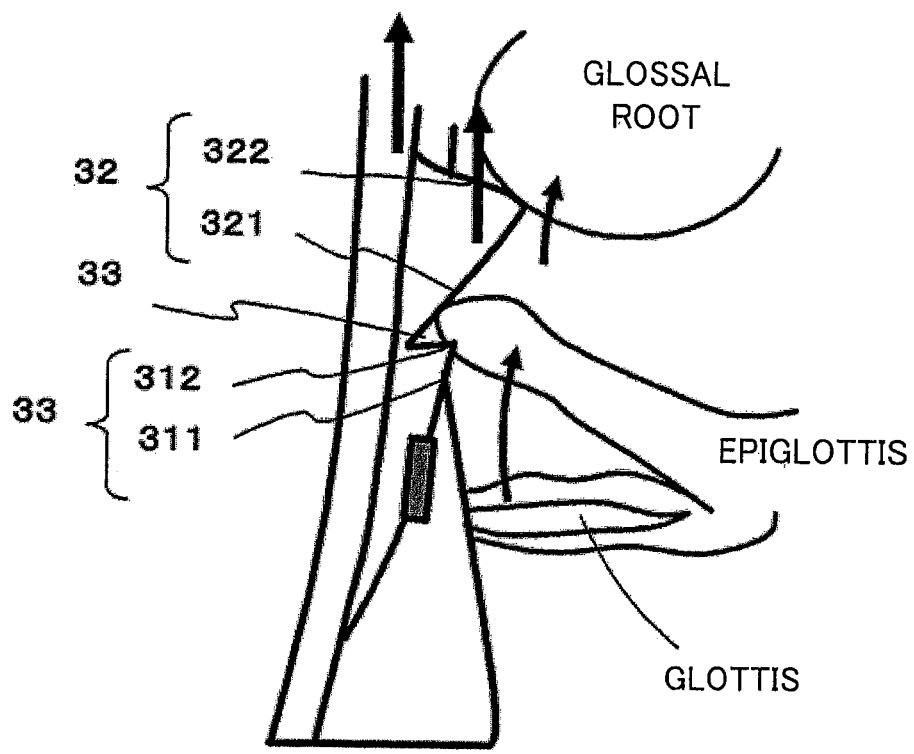
FIG. 7B is a second diagram showing the operation of the lifting body.

The following will describe an operation of the lifting body 30. FIGS. 7A and 7B are diagrams for simply describing the operation of the lifting body 30.

When the blade section 20 which is the tip is made to move ahead toward the esophagus, the blade section 20 passes the glossa, and further moves down while being adjoined to the glottis, the tracheal entrance. At this moment, the blade section 20 moves ahead like sliding while the inclined portions 311 of the first protruding portions 31 and the inclined portions 321 of the second protruding portions 32, which are provided on the lifting body 30 for making the blade section 20 pass easily through the glossal root and epiglottis, contact with the peripheral portions of the glossal root and the epiglottis. As a result of that, as shown in FIG. 7A, the epiglottis is on the first protruding portions 31, and further the glossal root is on the second protruding portions 32.

Next, as shown in FIG. 7B, when whole of the main body section 10 is pulled back upward, the hooking portions 312 of the first protruding portions 31 of the lifting body 30 hook and raise the epiglottis while contacting with the periphery of the epiglottis. Further, the hooking portions 322 of the second protruding portions 32 hook and raise the glossal root while contacting with the periphery of the glossal root. That is, in the process of pulling the main body section 10 back, the epiglottis is hooked and pushed up by the hooking portions 322, and thereby the glottis moves into an open state.

When the epiglottis is raised, the operator is allowed to view the glottis with the bronchial fiber 200 which is housed in the U-shaped groove 40.

As mentioned above, the present endotracheal intubation support instrument 100 is designed in such a way as to raise the epiglottis by the operation of the lifting body 30 even if the patient is in a state that the tracheal entrance is blocked by the epiglottis. Due to this, it is possible to open easily the tracheal entrance.

Next, the following will describe the bridge 50.

The bridge 50 has chips 50a and 50a provided in an inside region of the flap 22 in such a way as to extend from the banks of the U-shaped groove 40 toward the center respectively. The bridge 50 is formed so that the chips 50a and 50a face each other. At a position where the chips 50a and 50a faces each other, that is, at a vicinity of the central portion, a gap 51 is provided. Each of the chips 50a is flexible, thereby it is possible to spread out the gap between the chips 50a and 50a, that is, the gap 51. The bridge 50 is formed on an upper surface of the U-shaped groove 40. Thereby, the operator is allowed to put the tip of the bronchial fiber on the bridge 50 to use the bridge 50 as a board for turning the bronchial fiber toward an inside of the airway.

Figure 8A:
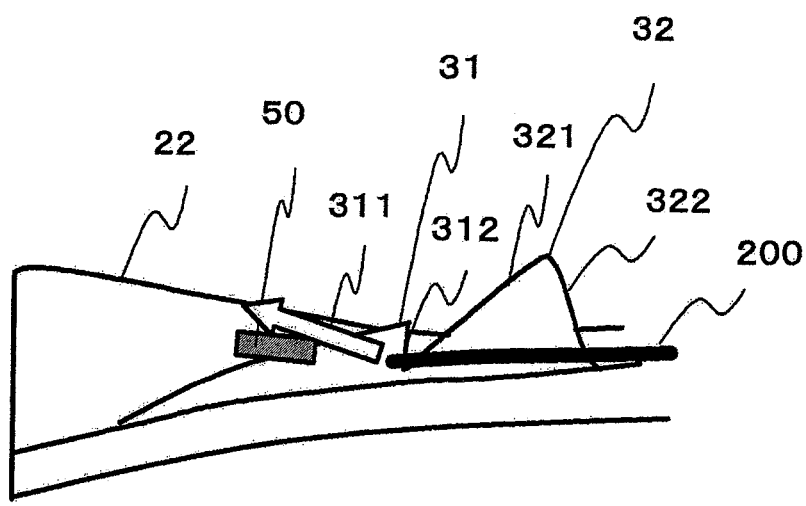
Figure 8B:
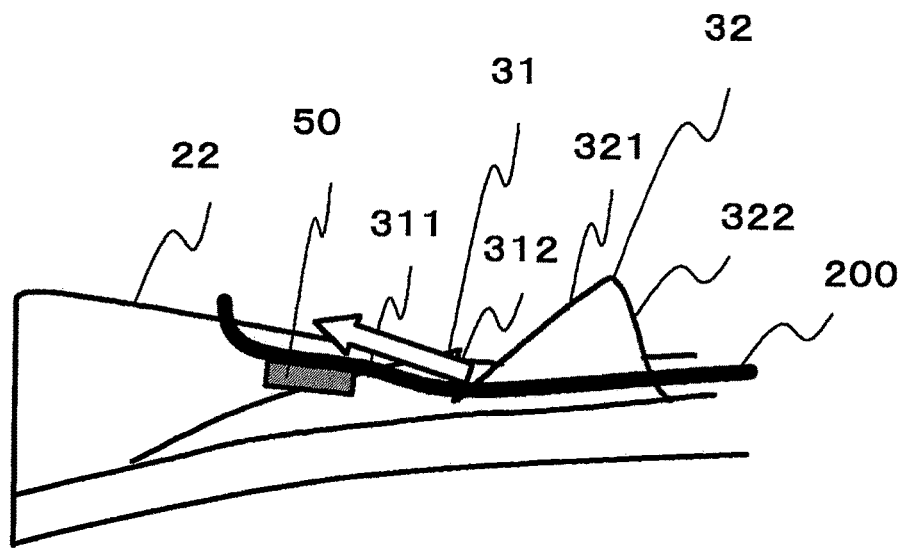
Figure 8C:
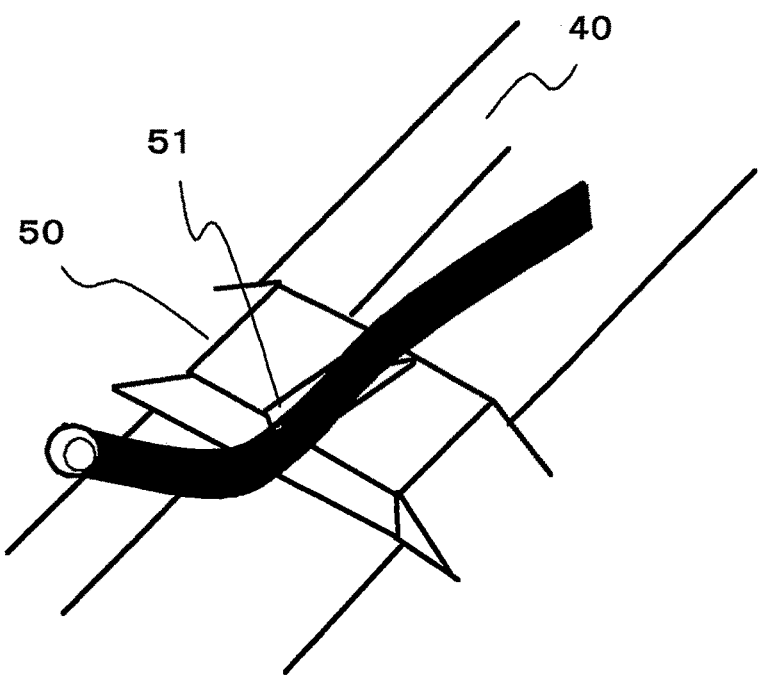

FIGS. 8A to 8C are diagrams for simply showing a state that the bridge 50 is used as a lift stand which is a kind of placing stand where the vicinity of the tip of the bronchial fiber 200 is placed on. Those diagrams are partial enlarged views of the vicinity of the blade section 20. FIGS. 8A and 8B are shown, as with FIGS. 5A and 5B, as vertical sectional views taken along line A-A of FIG. 3A.

In the intubation manipulation of the bronchial fiber 200, when the bronchial fiber 200 goes on along the inside of the U-shaped groove 40, as shown in FIG. 8A, at the forward position, the bridge 50 appears. Here, the operator should turns the tip of the bronchial fiber 200 upward, and move the bronchial fiber 200 so as to be put on the upper surface of the bridge 50. In other words, when the bronchial fiber 200 comes close to the vicinity of the bridge 50, the bronchial fiber 200 raises its head to get on the bridge 50 and move ahead. FIGS. 8B and 8C simply show a state that the bronchial fiber 200 has been put on the upper surface of the bridge 50.

Here, as shown in FIG. 4B, it is preferable that the gap 51 located at the vicinity of the central portion of the bridge 50 is provided obliquely against a center line CL of the U-shaped groove 40. In a state that the blade section 20 has been inserted to the vicinity of the tracheal entrance, when the flap 22 is spread out in a right-left direction because of the structures of organs of the patient, the right and left chips 50a and 50a constituting the bridge 50 are sometimes separated from each other widely. In this state, if the gap 51 of the bridge 50 is provided in a parallel with the center line CL of the U-shaped groove 40 and the space of the gap 51 is big, the bronchial fiber 200 would drop down through the gap 51, and thereby the bridge 50 would not function as a pedestal, that is, the lift stand. However, if the gap 51 is provided obliquely against the center line CL of the U-shaped groove 40, the bridge 50 can function as the lift stand for the bronchial fiber 200 more reliably.

The following will describe a case that the bronchial fiber 200 passes under the bridge 50, without getting on the bridge 50.

Under the bridge 50, there is a cavity Ca (see FIG. 3A) having a size enable the bronchial fiber 200 to pass through and communicating with the U-shaped groove 40. The bronchial fiber 200 is allowed to pass under the bridge 50 to move ahead by going through the cavity Ca existing under the bridge 50. The bronchial fiber 200 should take this route, in a case that the bronchial fiber 200 can reach the trachea more easily if moving ahead by passing under the bridge 50 because of a positional relation and an angular relation between the blade section 20 and the trachea of the patient. At an actual scene of tracheal intubation treatment, there would be various cases. So, the above case would happen. In this case, the bridge 50 is located between the tracheal entrance portion and the epiglottis, and thereby the bridge 50 can work for separating the epiglottis from the tracheal entrance to establish the viewing filed of the bronchial fiber 200.

Figure 9C:
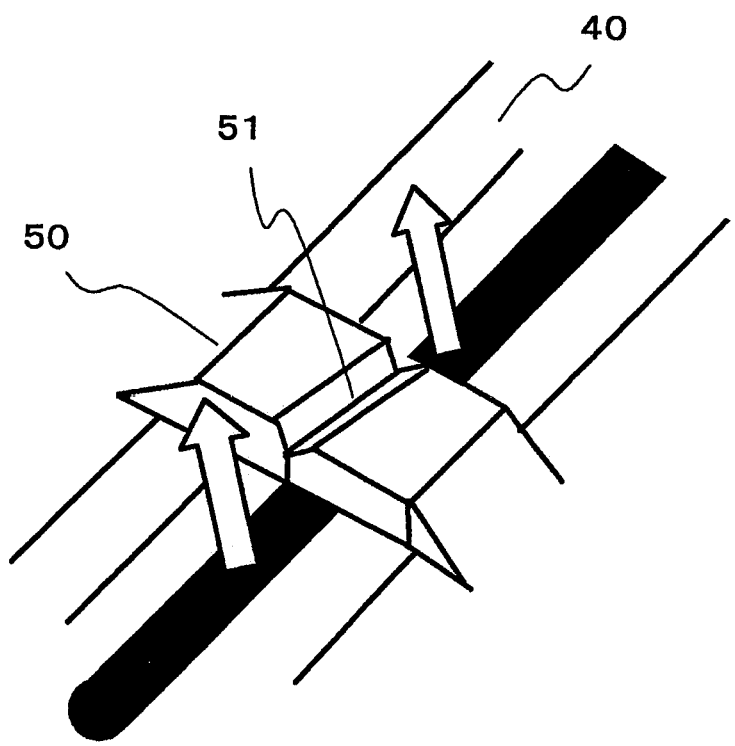
FIG. 9C is a third diagram which simply shows procedure that the tip of the bronchial fiber is made to pass under the bridge and move ahead, and thereafter, the endotracheal intubation support instrument of the present invention is pulled out.

FIGS. 9A to 9D are diagrams for simply showing procedures for making the tip of the bronchial fiber 200 pass under the bridge 50 and move ahead, and thereafter pulling out the present endotracheal intubation support instrument 100. FIGS. 9A to 9D are partial enlarged views of the vicinity of the blade section 20. FIGS. 9A and 9B are shown, as with FIGS. 5A and 5B, as vertical sectional views taken along line A-A of FIG. 3A.

FIG. 9A simply shows a state that the tip of the bronchial fiber 200 is made to pass under the bridge 50 and move ahead. This case is that in the state shown in FIG. 9A the glottis is found by means of the bronchial fiber 200, and, from this state, the bronchial fiber 200 is made to further move ahead to pass through the glottis, and is finally inserted to the trachea.

FIG. 9B is a diagram showing a state that while the bronchial fiber 200 inserted to the trachea is left, only the present endotracheal intubation support instrument 100 is pulled out.

The two chips 50a and 50a, a right side one and left side one of the bridge 50 respectively, facing each other have flexibility. If external force is applied on the bridge 50, the chips 50a and 50a are bent and the gap of the bridge 50, that is, the gap 51 is made wider. Accordingly, even if the present endotracheal intubation support instrument 100 is pulled out in a state the bronchial fiber 200 has passed under the bridge 50 to be inserted to the trachea, the bridge 50 is easily widen and removed from the bronchial fiber 200. Therefore, it is possible to pull out the present endotracheal intubation support instrument 100 with no influence on the insertion state of the bronchial fiber.

Figure 9D:
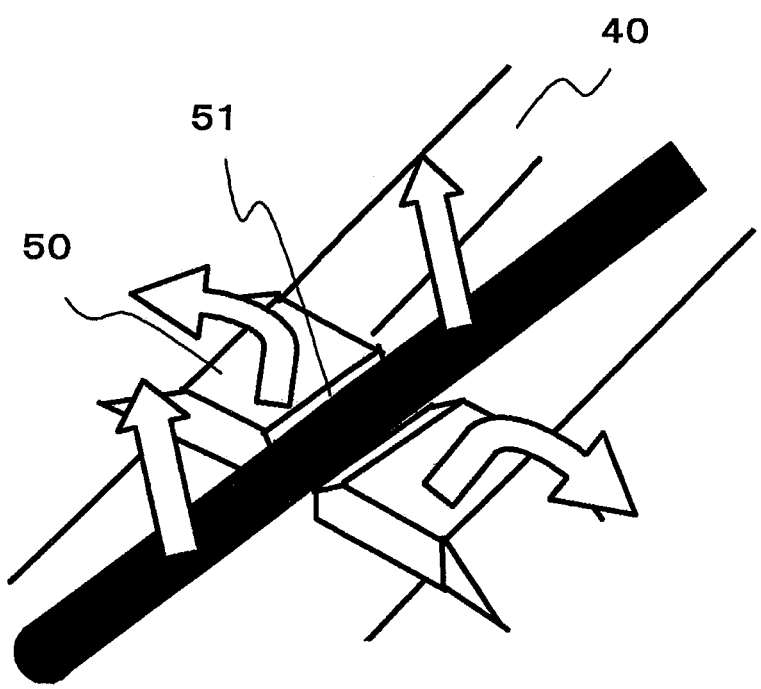
FIG. 9D is a fourth diagram which simply shows procedure that the tip of the bronchial fiber is made to pass under the bridge and move ahead, and thereafter, the endotracheal intubation support instrument of the present invention is pulled out.

FIGS. 9C and 9D are diagrams for descriptions of open and close of the bridge 50 and switching between a fixed state and a removed state, each of which is a state of the bronchial fiber 200 to the U-shaped groove 40.

FIG. 9C shows a state that the bronchial fiber 200 still stays in the U-shaped groove 40, but the bronchial fiber 200 is going to be removed upward. In FIG. 9C, the bronchial fiber 200 still blocks the upper surface of the U-shaped groove 40. That is, in a state that external force is not applied, the gap 51 is smaller than the diameter of the bronchial fiber 200.

FIG. 9(d) shows a removed state of the bronchial fiber 200 removed from the U-shaped groove 40. The bridge 50 has flexibility and can be deformed. Due to this, when the bronchial fiber 200 is manipulated so as to pass through the bridge 50 from a lower surface side to an upper surface side thereof, the gap 51 between the chips 50a and 50a, the right and left side ones of the bridge 50, is spread out, and thereby the bronchial fiber 200 can pass through the gap 51 and thereby can be removed from the U-shaped groove 40.

The above is a description for one of configuration examples of the bridge. It is possible to set arbitrarily whether the gap 51 is provided or not, and what shape the gap 51 has.

Next, the following will describe the handle section 60. The handle section 60 is located at the user side when the operator uses the present endotracheal intubation support instrument 100. The handle section 60 is viewed as a shape of the operator side of the main body section 10. In this configuration example, provided to the main body section 10 is the handle section 60 elliptically spreading like a rice scoop for helping the operator hold.

In other words, the handle section 60 has a shape elliptically and flatly spreading toward the end portion. The handle section 60 helps the operator grasp, thereby it becomes easy for the operator to manipulate the whole of the present endotracheal intubation support instrument 100. Especially, important for the present endotracheal intubation support instrument 100 is a function which raises the epiglottis by the lifting body 30 in order to secure the airway for a patient whose tracheal entrance is blocked by the epiglottis. Accordingly, as a manipulation to the present endotracheal intubation support instrument 100, conceived is hooking the epiglottis to raise the epiglottis by the lifting body 30. If the handle section 60 is prepared, such a manipulation is possible to be easily performed.

Figure 10:
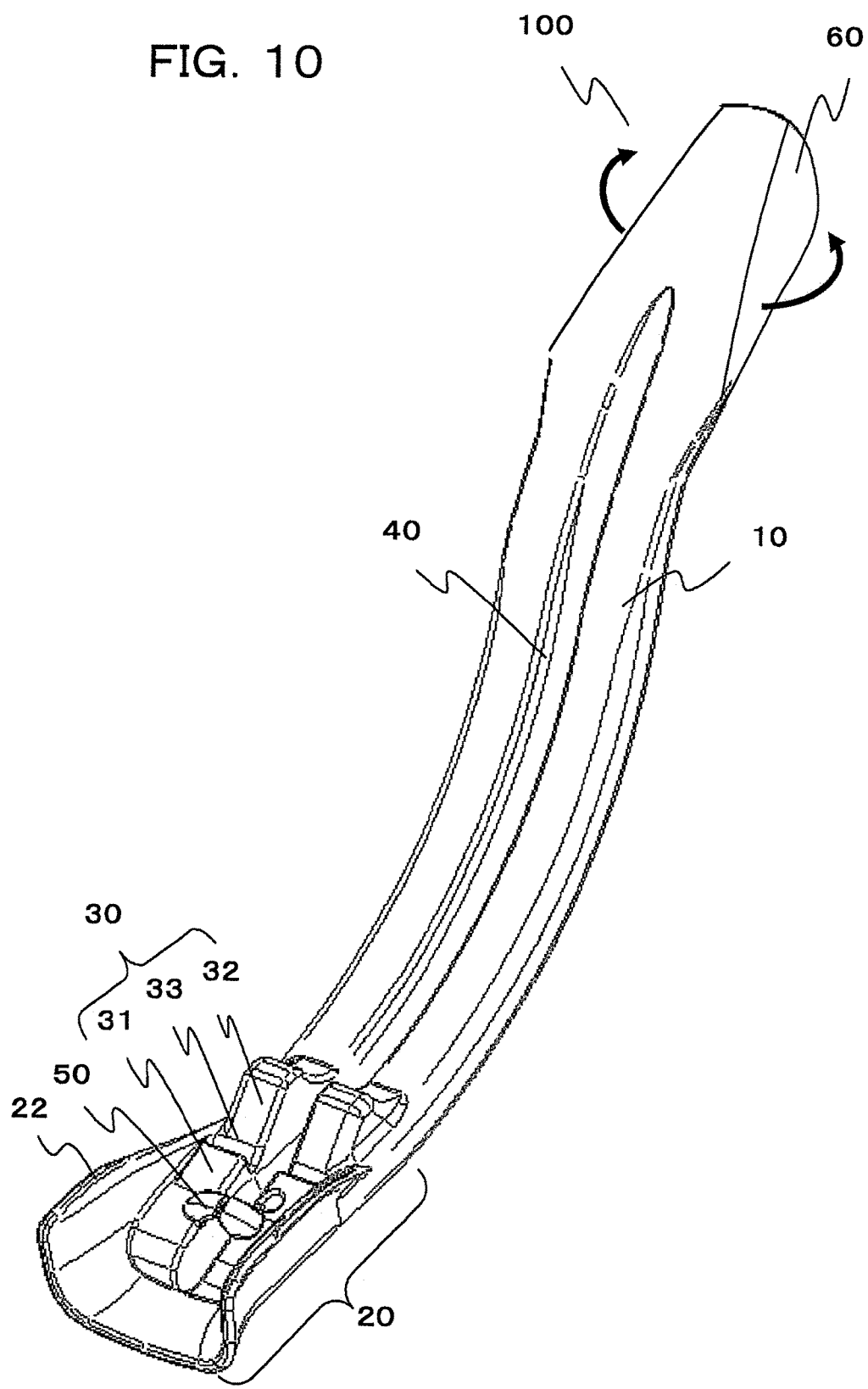
FIG. 10 is a first diagram simply showing a state which a handle section has been transmuted into a compact size by folding a thin portion of the handle section along folding grooves.

One example of a distinctive point in the shape of the handle section 60 will be shown. As shown in FIGS. 1, 2, and 4A, the distinctive point is: the main body section 10 has a structure getting thinner gradually toward the handle section 60, and a thin portion is provided in such a way as to be easily bent and curled. Further, as shown FIGS. 2 and 3B, it is preferable that grooves 61 for fold are provided on a back surface of the handle section 60. As mentioned later, when the patient is treated, in a case that procedures of putting an oxygen mask on the patient and oxygenating sufficiently an inside of his/her body should be executed prior to the manipulation for inserting the bronchial fiber 200, it is necessary to put the oxygen mask on the patient whom the present endotracheal intubation support instrument 100 has been inserted to. At this moment, if the thin portion of the handle section 60 can be easily bent or curled as shown in FIG. 10, the handle section 60 is compactly put in the mask. Thereby, as shown in FIG. 14B, the oxygen mask 400 and the patient are in close contact with each other. Therefore, artificial ventilation is possible. At this moment, the present endotracheal intubation support instrument 100 works for opening the airway from the mouth up to the tracheal entrance. In this example, the handle section 60 is formed in an elliptically spread shape like a rice scoop, and the thin portion of the handle section 60 can be folded along the grooves 61 as shown in FIG. 10. With respect to a design of the handle section 60, as long as easily holding is secured, the handle section 60 may have, to begin with, a sterically folded shape as shown in FIG. 10, for making the length smaller with respect to its width direction.

The above described one configuration example of the handle section. However, the shape, thickness, and grooves for fold of the handle section are not limited to the above example, and are allowed to be set arbitrarily.

Next, the following will describe the suction tube 70.

The suction tube 70 works as a suction passage for securing a viewing field, after the insertion of the present endotracheal intubation support instrument 100 and prior to the insertion of the bronchial fiber, by removing body fluid including saliva and blood which could be an obstacle against the viewing field of a finder, water vapor causing fog, and the like.

As shown in FIGS. 2 and 3B, the suction tube 70 which is a body of the suction passage is arranged along the back surface of the main body section 10 and allowed to pass through the blade section 20 from its back surface to its front surface.

FIG. 6A is a diagram showing a vertical sectional view taken along line B-B of FIG. 3A, and shows a sectional view of a portion where the suction tube 70 is being provided.

As shown in FIG. 6A, a tip of the suction tube 70 opens by penetrating the flap 22 of the blade section 20 from its back surface to its front surface. The back end side of the suction tube 70 is attached to the back surface side of the handle section 60. The suction tube 70 is arranged in such a way as to run thorough the blade section 20, the main body section 10, and the handle section 60.

As comprehensively shown in FIGS. 2 and 6A, an engagement groove 71 for engaging with the suction tube 70 is provided on the back surface of the handle section 60. In this configuration example, the engagement groove 71 comprises right and left chips. The gap of the engagement groove 71 corresponds to the outer diameter of the suction tube 70. The engagement groove 71 is configured to sandwich the suction tube 70 so that the suction tube 70 is attached to the engagement groove 71.

The above is a description for one of configuration examples of the suction tube. However, the suction passage is not limited to this configuration example. The suction passage may be built in either the blade section, the main body section, or the handle section. Further, the number of suction passages and the position of each suction passage are allowed to be set arbitrarily.

The above is a simple description of each component of the present endotracheal intubation support instrument 100.

Next, the following will describe a method for using the present endotracheal intubation support instrument 100.

The method for using the present endotracheal intubation support instrument 100 is allowed to be selected depending on the situation by the determination of each scene. Here, as one example of methods for using it, procedures for executing a sequence of manipulations for intubation with the present endotracheal intubation support instrument 100 will be described. After inserting the present endotracheal intubation support instrument 100 to the larynx from the oral cavity of the patient, prior to the insertion of the bronchial fiber, artificial ventilation is executed using the oxygen mask and the present endotracheal intubation support instrument 100 as the airway. Then, after oxygen is sufficiently supplied to the patient, the sequence of manipulations for intubation is executed.

Figure 11A:
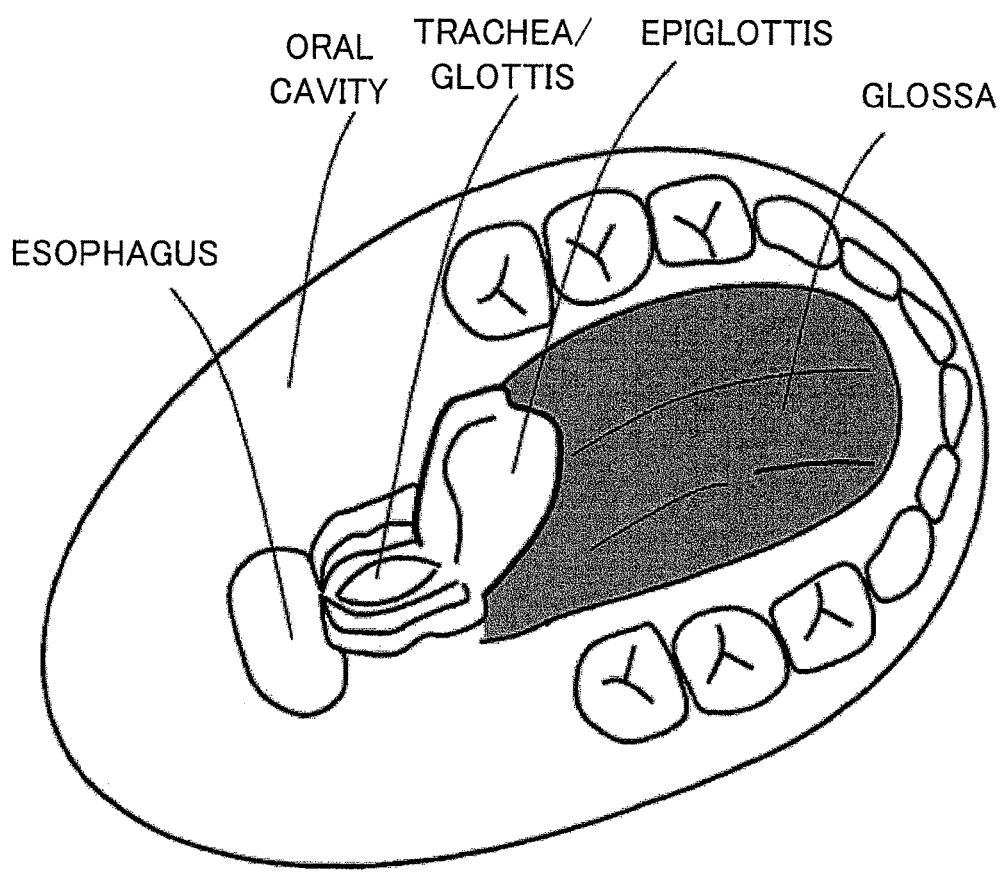
FIG. 11A is a first diagram showing simply as much as possible structures of an oral cavity, trachea, epiglottis, esophageal entrance, and the like of a general patient.
Figure 11B:
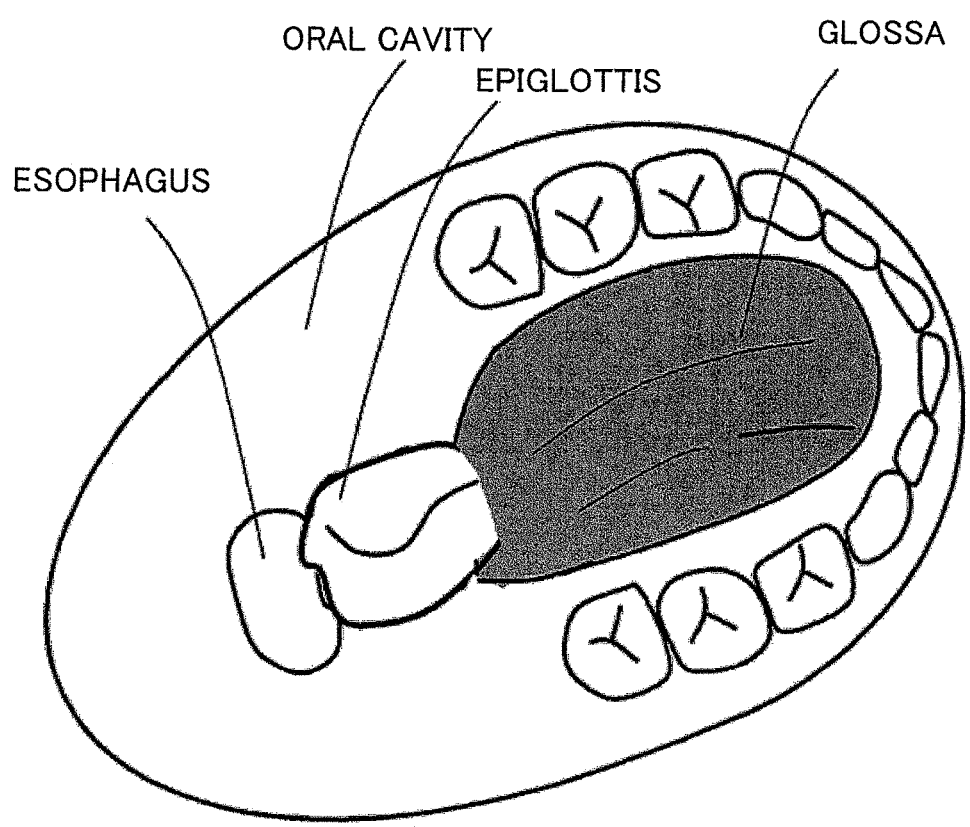
FIG. 11B is a second diagram showing simply as much as possible the structures of the oral cavity, trachea, epiglottis, esophageal entrance, and the like of the general patient.

FIGS. 11A and 11B are diagrams simply showing the structures of the oral cavity, trachea, epiglottis, esophageal entrance, and the like of a general patient. As shown in these diagrams, in the oral cavity, the glossa exists, and in a deeper position than the glossa, the epiglottis exists. The epiglottis functions as a lid which opens and closes the tracheal entrance.

FIG. 11A shows a state that the epiglottis is raised, and the glottis existing at the tracheal entrance can be viewed. FIG. 11B shows a state that the epiglottis closes the tracheal entrance.

Figure 12A:
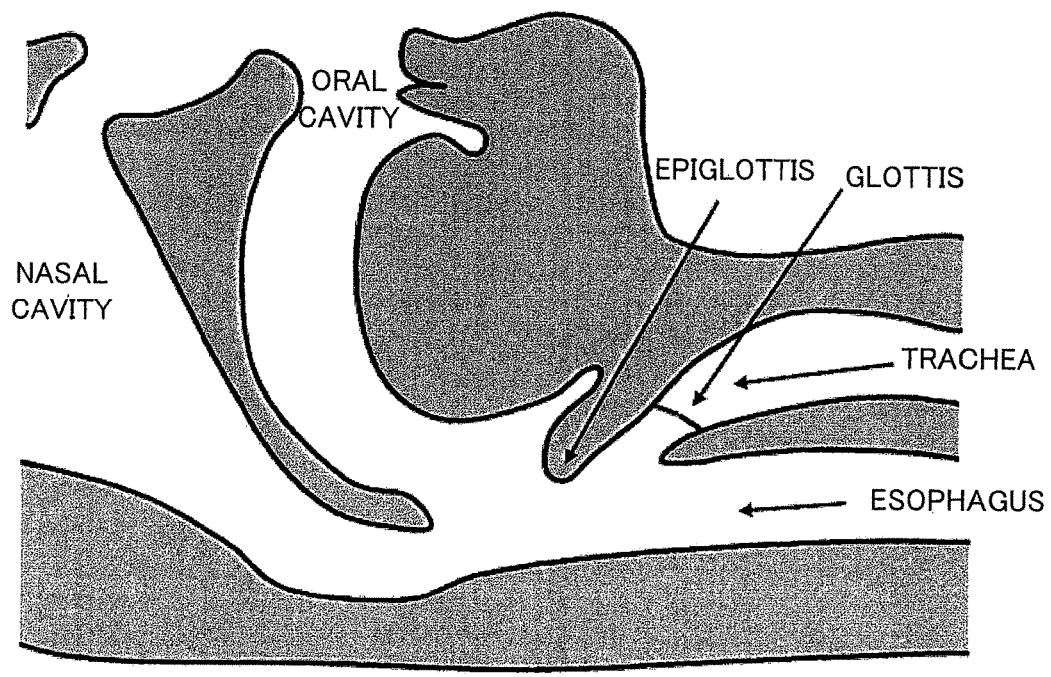
FIG. 12A is a first diagram showing a simple median cross-sectional view of a nasal cavity, oral cavity, pharynx, larynx, trachea, and vicinity of an esophagus of a human body.
Figure 12B:
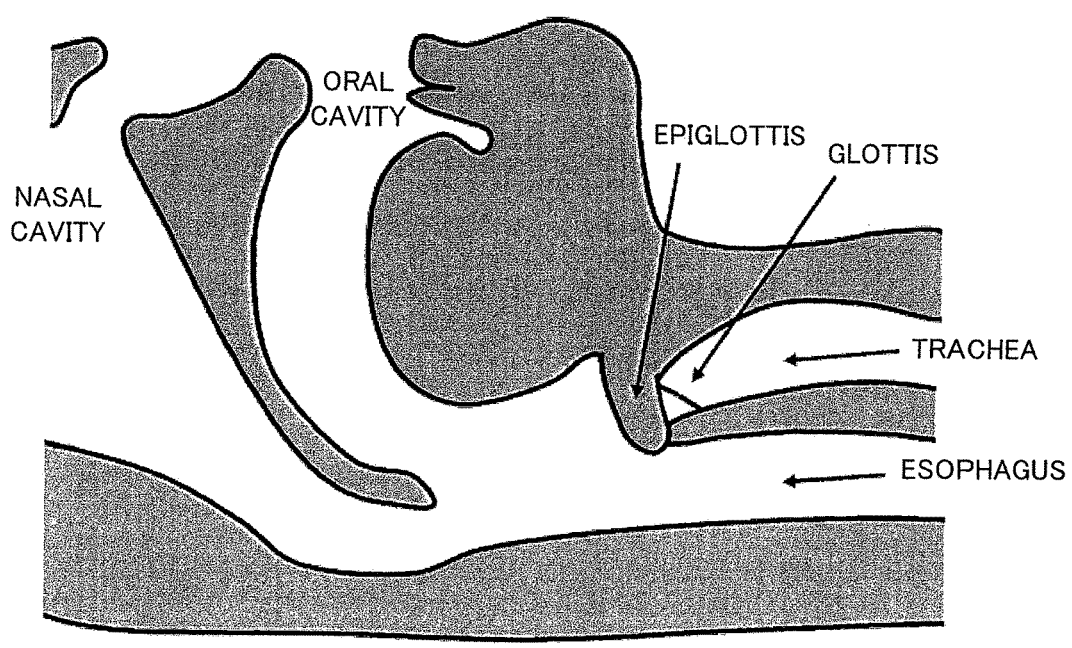
FIG. 12B is a second diagram showing a simple median cross-sectional view of the nasal cavity, oral cavity, pharynx, larynx, trachea, and vicinity of an esophagus of a human body.

FIGS. 12A and 12B are diagrams each simply showing a medium cross-sectional view of the nasal cavity, oral cavity, pharynx, larynx, trachea, and vicinity of the esophagus of a human body. FIG. 12A shows a state that the epiglottis is raised thereby the tracheal entrance is opened. FIG. 12B shows a state that the epiglottis closes the tracheal entrance.

In a case of an operative procedure for securing the airway of an unconscious patient, if the epiglottis is being raised as shown in FIGS. 11A and 12A, the treatment may be continued with such a state of the epiglottis. However, in a case of a patient whose epiglottis is closing the tracheal entrance as shown in FIGS. 11B and 12B, first it is necessary to raise the epiglottis.

Figure 13A:
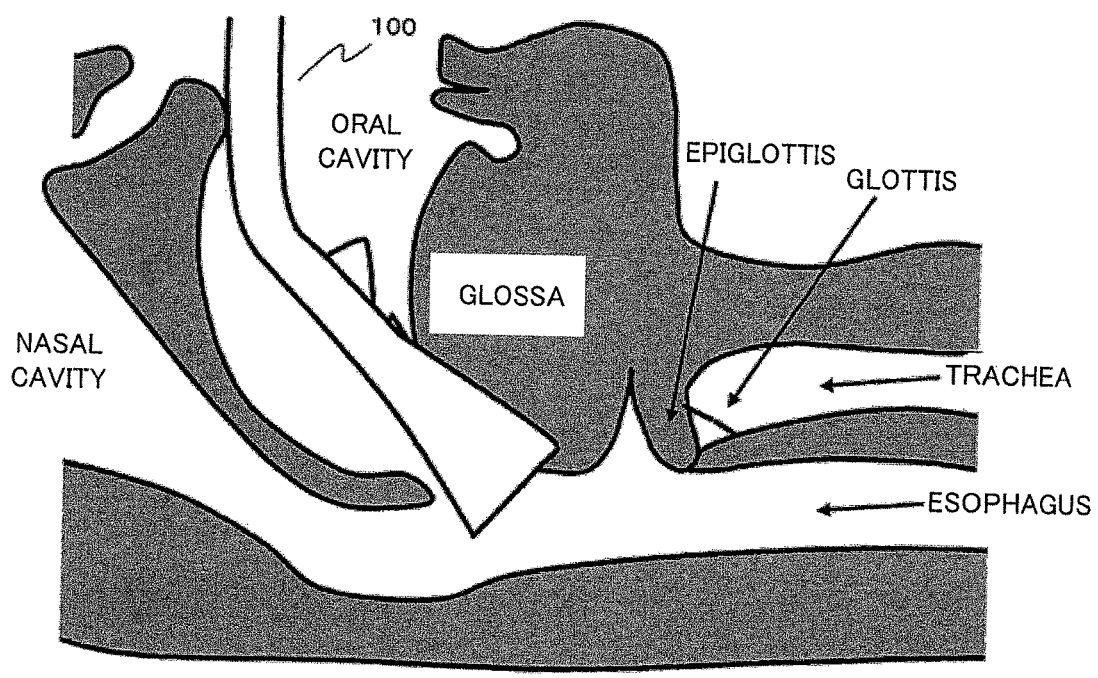
FIG. 13A is a first diagram showing a state the endotracheal intubation support instrument of the present invention is inserted into the esophageal entrance from the oral cavity together with the bronchial fiber housed in the U-shaped groove.
Figure 13B:
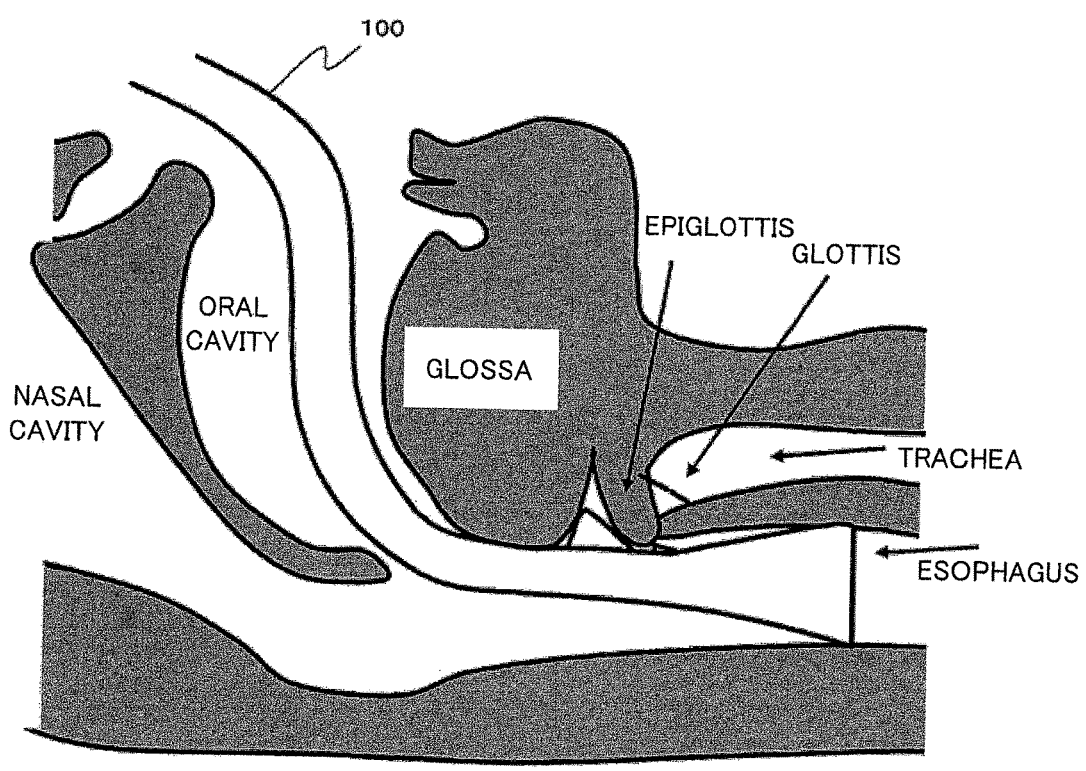
FIG. 13B is a second diagram showing a state the endotracheal intubation support instrument of the present invention is inserted into the esophageal entrance from the oral cavity together with the bronchial fiber housed in the U-shaped groove.

FIGS. 13A and 13B are diagrams showing a state that the present endotracheal intubation support instrument 100 is being inserted to the larynx from the oral cavity. As shown in these diagrams, if the operator makes the present endotracheal intubation support instrument 100 just move ahead from the oral cavity to the pharynx, the blade section 20 is inserted to a position near the trachea. It is possible to quickly provide this state to the operator by means of the present endotracheal intubation support instrument 100.

As a posture of the present endotracheal intubation support instrument 100 during that insertion, the present endotracheal intubation support instrument 100 should be inserted to the oral cavity in such a posture that the U-shaped groove 40 is located on the tracheal side.

As a result of that, as shown in FIG. 13B, when the tip of the main body section 10 reaches the vicinity of the trachea, the lifting body 30 is located at a position facing the epiglottis.

Figure 14A:
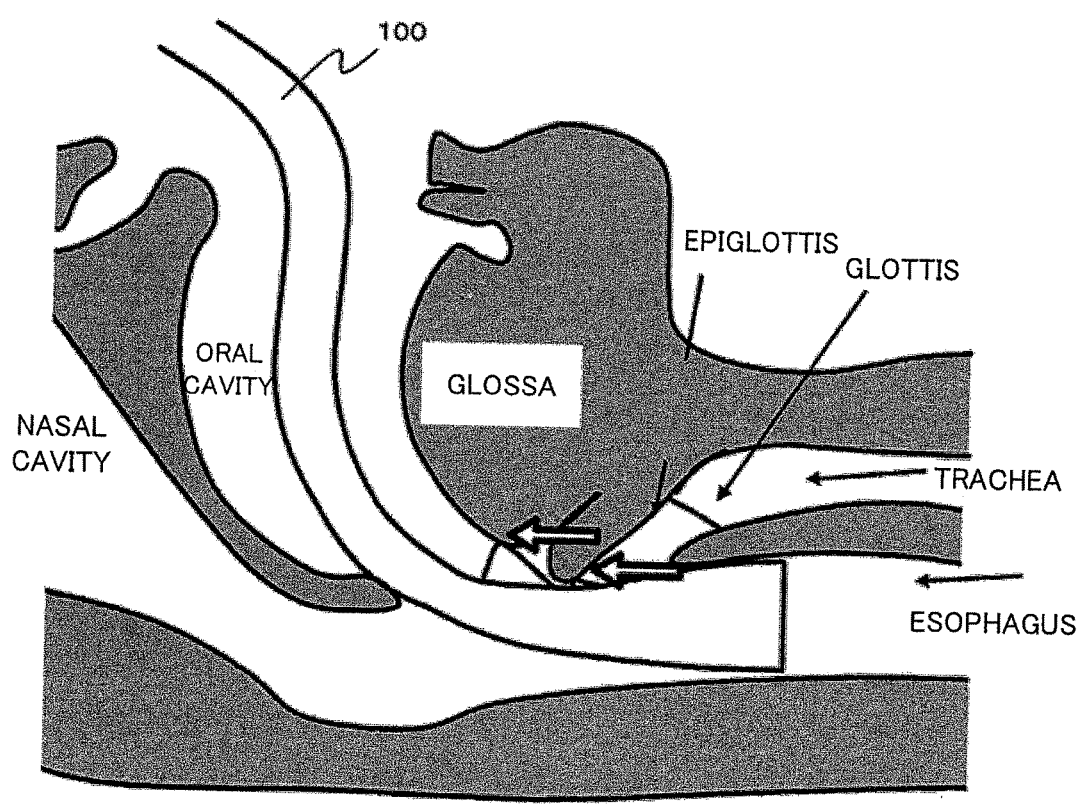
FIG. 14A is a diagram showing a state that the endotracheal intubation support instrument of the present invention is pulled back to raise the epiglottis.
Figure 14B:
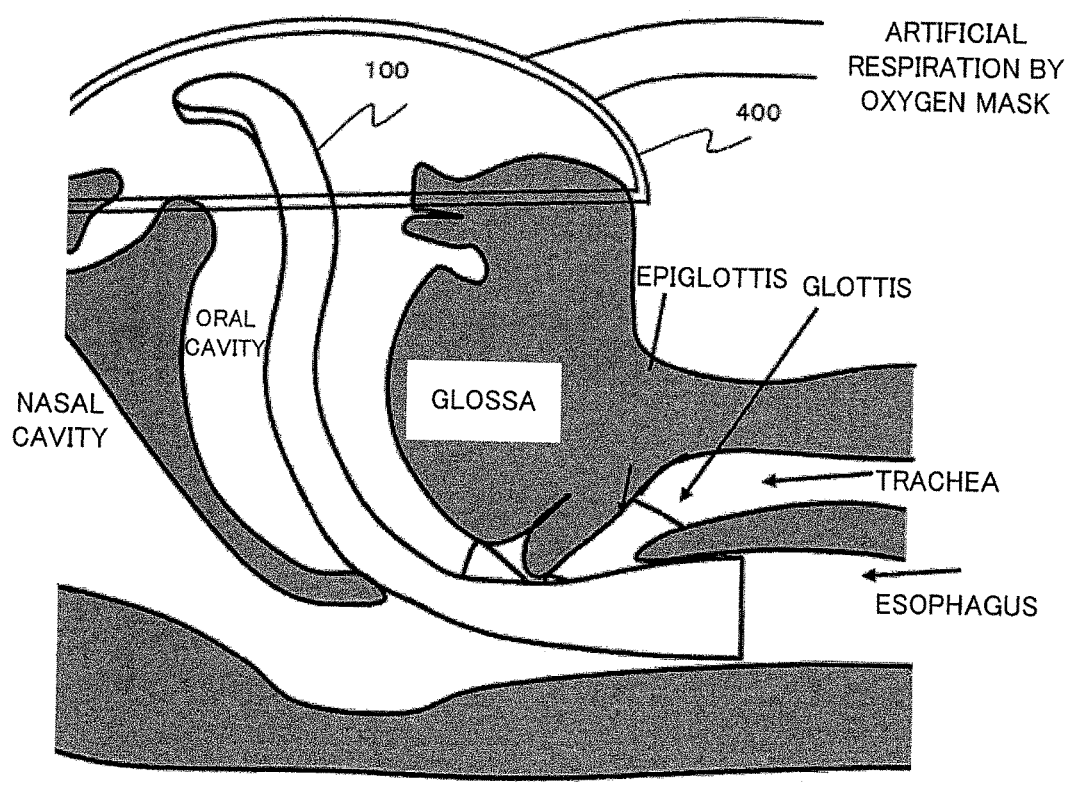
FIG. 14B is a diagram showing a state of artificial ventilation using an oxygen mask.

Next, FIG. 14A is a diagram showing a state that the epiglottis is raised by means of the present endotracheal intubation support instrument 100.

As mentioned above, in accordance with the operation for raising the epiglottis by using the lifting body 30, in manner of FIG. 7, the operator should move slowly the present endotracheal intubation support instrument 100 upward to hook and raise the epiglottis by the lifting body 30. The lifting body 30 is located at a position facing the epiglottis. Therefore, in this state, when the operator moves slowly the blade section 20 in a vertical direction via the main body section 10, the tips of the first protruding portions 31 of the lifting body 30 contact with the periphery of the epiglottis. Thereby, it is possible to raise the epiglottis by hooking the vicinity of the tip of the epiglottis. The tips of the second protruding portions 32 contact with the periphery of the glossal root, thereby it is possible to hook and raise the glossal root.

In a case that the operator just squeezes the present endotracheal intubation support instrument 100 to make the support instrument 100 move ahead to a deeper position than the pharynx from the oral cavity, the epiglottis and glossal root are often raised automatically, as shown in FIG. 13A, by the inclined portions 311 and inclined portions 312 of the lifting body 30. Therefore, the mentioned operation for raising the epiglottis should be executed if necessary, in a case that respiration is not active even after the insertion of the present endotracheal intubation support instrument 100.

Here, prior to the intubation of the bronchial fiber 200, the artificial ventilation using the oxygen mask is available. In the state shown in FIG. 14A, the epiglottis has been already raised, and the present endotracheal intubation support instrument 100 has been already inserted up to a position near the glottis from the oral cavity. Accordingly, the U-shaped groove 40 is available as the airway extending from the oral cavity up to the glottis. The patient may be in a state that his/her breathing is not secured. Therefore, it is preferable to support his/her breathing as early as possible. Therefore, as shown in FIG. 14B, prior to the intubation of the endotracheal tube, first, the oxygen mask 400 should be put on the patient and the artificial ventilation should be tried.

After the oxygen mask 400 is put on the patient, oxygen should be forcibly sent to the trachea of the patient from an artificial ventilator not illustrated. It is possible to expect a lot of cases the patient's respiration can be secured by this artificial ventilation.

As shown in FIG. 14B, the length of the present endotracheal intubation support instrument 100 is adjusted so that the present endotracheal intubation support instrument 100 does not protrude from the oxygen mask 400 which has been put on the patient. Also, the shape of the handle section 60 is adjusted. For example, the following designs could be applied: the handle section 60 gradually gets thinner from the main body section 10 to the handle section 60 and the thin portion is configured in such a way as to be easily bent and curled; or the grooves 61 for fold are provided on the back surface of the handle section 60. When the treatment is going to be started for the patient, in a case that, prior to the manipulation for intubation of the bronchial fiber 200, the following procedures should be required: putting the oxygen mask on the patient, and supplying oxygen sufficiently to the patient in order to heighten the oxygen level in blood, it is necessary to put the oxygen mask on the patient to whom the present endotracheal intubation support instrument 100 has been inserted. At this moment, if the thin portion of the handle section 60 can be easily bent or curled as shown in FIG. 10, the handle section 60 is compactly put housed in the oxygen mask. Thereby, the oxygen mask 400 is never floated.

After the artificial ventilation is executed for necessary time, the sequence goes to the manipulation for intubation of the bronchial fiber 200.

Figure 15A:
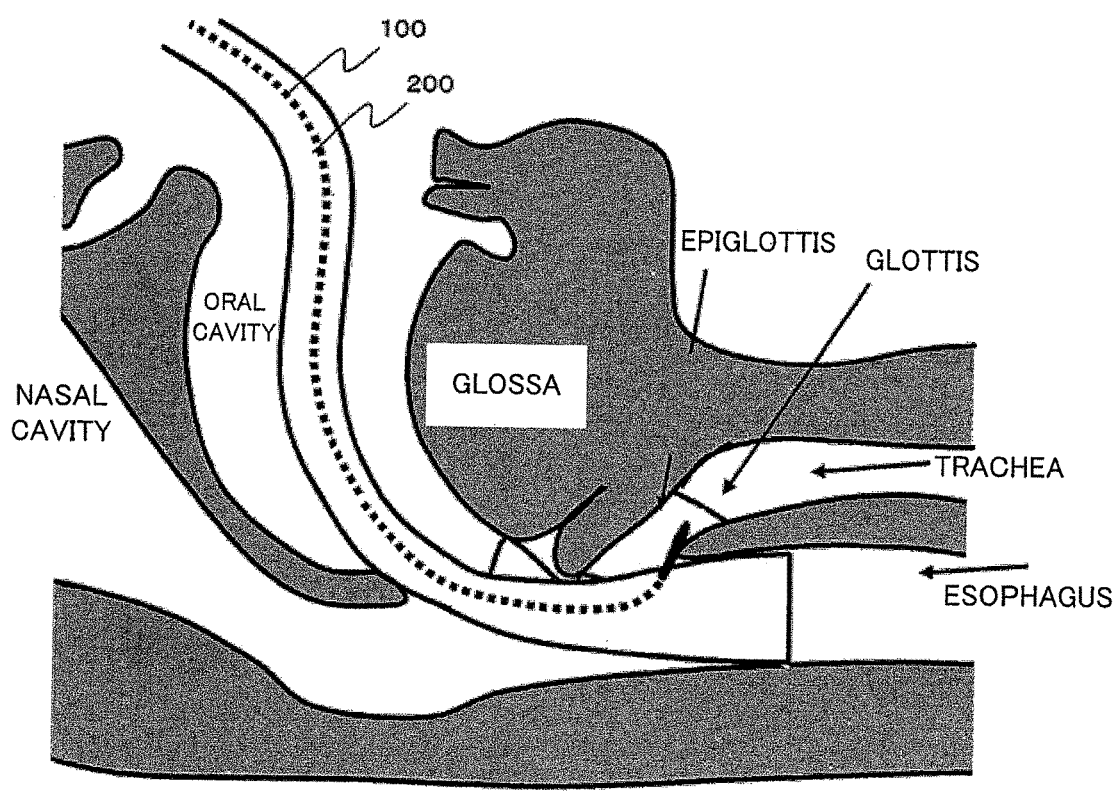
FIG. 15A is a first diagram showing a state that an operator is inserting the bronchial fiber into the trachea while checking the glottis by the bronchial fiber, after raising the epiglottis by the endotracheal intubation support instrument of the present invention.
Figure 15B:
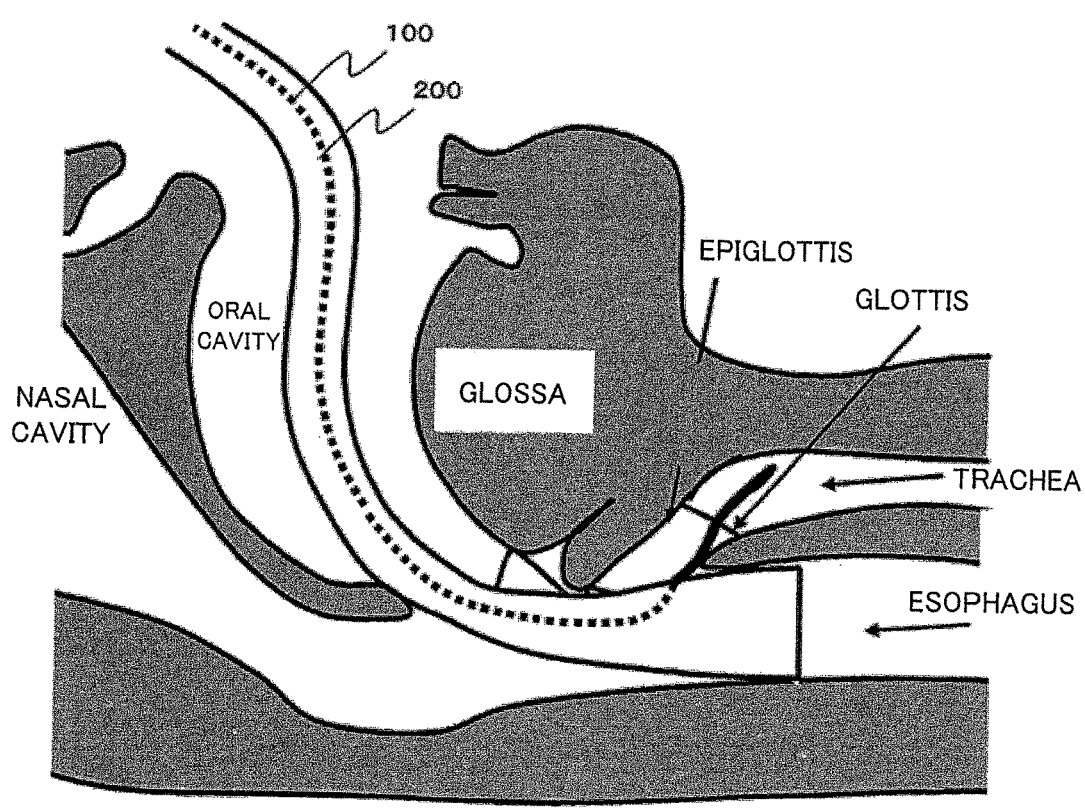
FIG. 15B is a second diagram showing the state that the operator is inserting the bronchial fiber into the trachea while checking the glottis by the bronchial fiber, after raising the epiglottis by the endotracheal intubation support instrument of the present invention.

FIGS. 15A and 15B are diagrams showing a state that the bronchial fiber 200 is being inserted using the U-shaped groove 40 as a passage, and then the bronchial fiber 200 is entering the trachea while the glottis is being viewed.

As shown in FIG. 15A, when the tip of the bronchial fiber 200 reaches the blade section 20, the glottis becomes possible to be viewed in the viewing field of the scope of the bronchial fiber 200.

Subsequently, as shown in FIG. 15B, by manipulating a guide wire of the bronchial fiber 200, when the bronchial fiber 200 moves ahead while bending the tip of the bronchial fiber 200 upward and its flexible tube is raised using the bridge 50 as the lift stand to turn for direction, the bronchial fiber 200 is possible to move further ahead to an inside of the glottis.

At this moment, since the width of the U-shaped groove 40 is larger than the outer diameter of the bronchial fiber 200, the bronchial fiber 200 is allowed to easily remove from the present endotracheal intubation support instrument 100.

Figure 16:
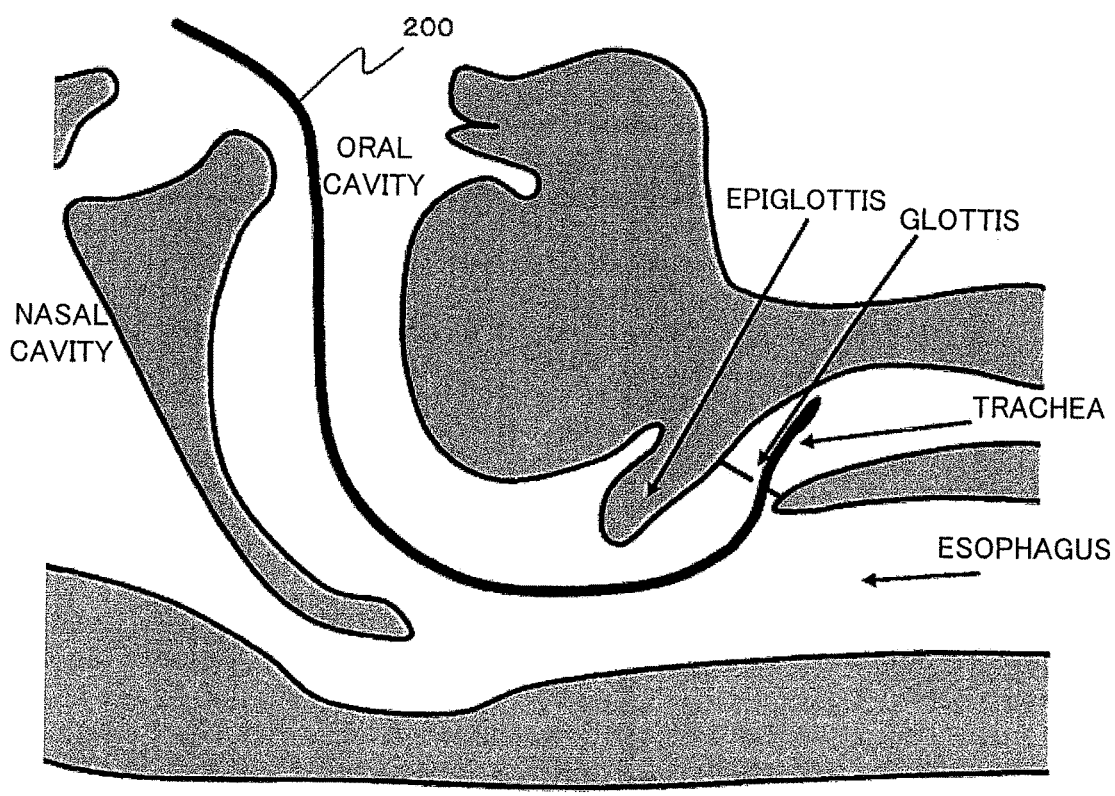
FIG. 16 is a diagram showing a state that the endotracheal intubation support instrument of the present invention has been pulled out from the oral cavity, pharynx, larynx and inside of the esophagus, and only the bronchial fiber is remained and is inserted into the trachea.

FIG. 16 is a diagram showing a state that the present endotracheal intubation support instrument 100 was pulled out from the body, and only the bronchial fiber 200 which was housed in the U-shaped groove 40 is left.

Since the present endotracheal intubation support instrument 100 has already accomplished its purpose, the present endotracheal intubation support instrument 100 in the state shown in FIG. 15B is slowly pulled out from the oral cavity. FIG. 16 shows a state that the present endotracheal intubation support instrument 100 was pulled out completely.

In the state of FIG. 16, only the bronchial fiber 200 is inserted to the trachea. However, the endotracheal tube 300 shown in FIGS. 17A and 17B has not yet been inserted. Due to this, it is necessary that the endotracheal tube 300 is inserted to the trachea using the bronchial fiber 200 as a guide. In this case, the procedure to be executed next is shown in FIG. 17A.

Figure 17A:
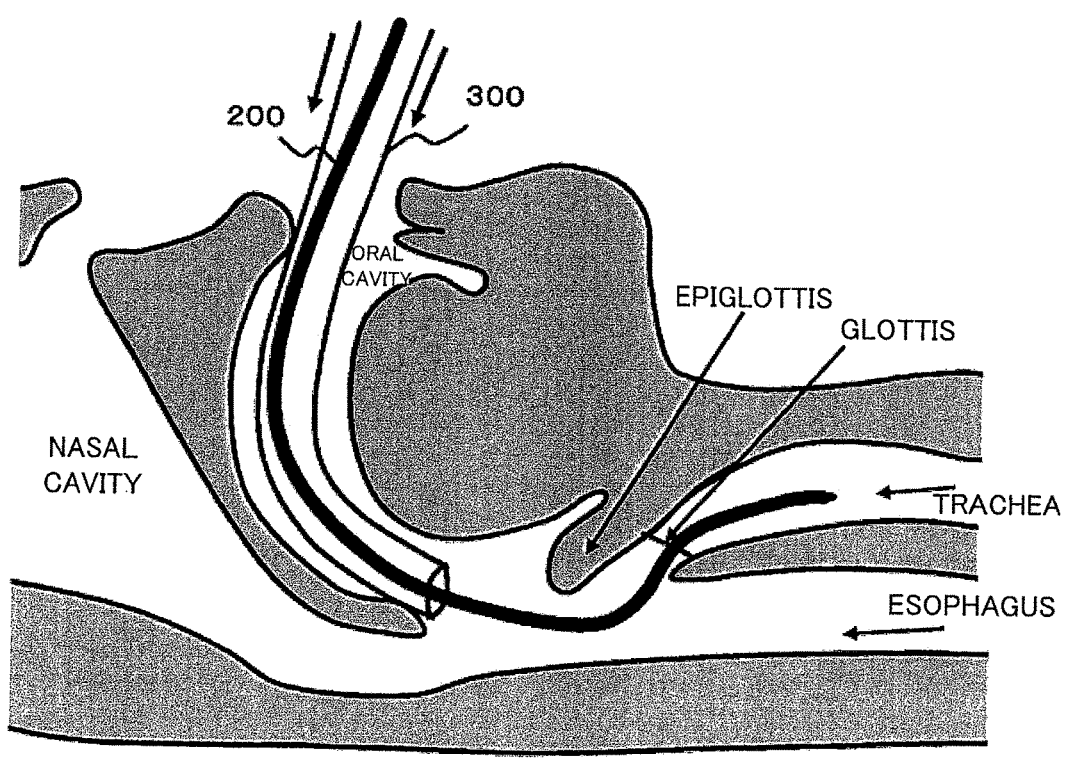
FIG. 17A is a diagram showing a state that the endotracheal tube is being intubated using the bronchial fiber as a guide.
Figure 17B:
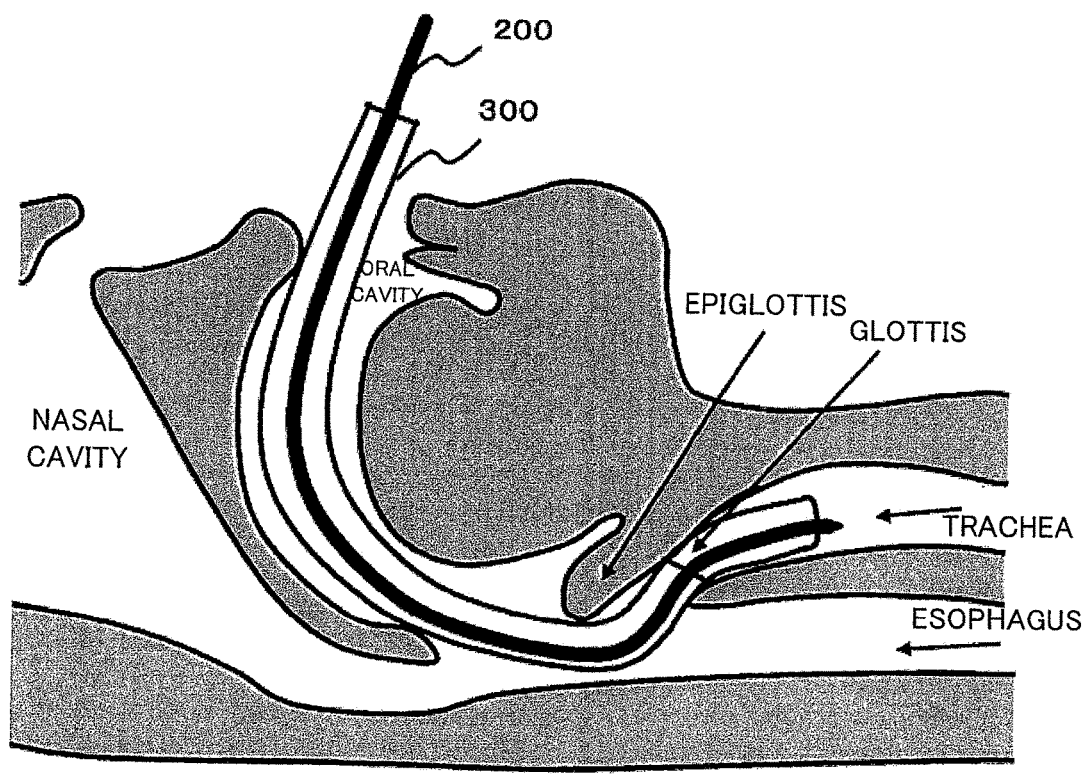
FIG. 17B is a diagram showing a state that the endotracheal tube has been inserted into the trachea completely.

FIG. 17A is a diagram showing a state that the endotracheal tube 300 is being intubated using the bronchial fiber 200 as a guide. FIG. 17B is a diagram showing a state that the endotracheal tube 300 is inserted into the trachea completely.

Figure 18A:
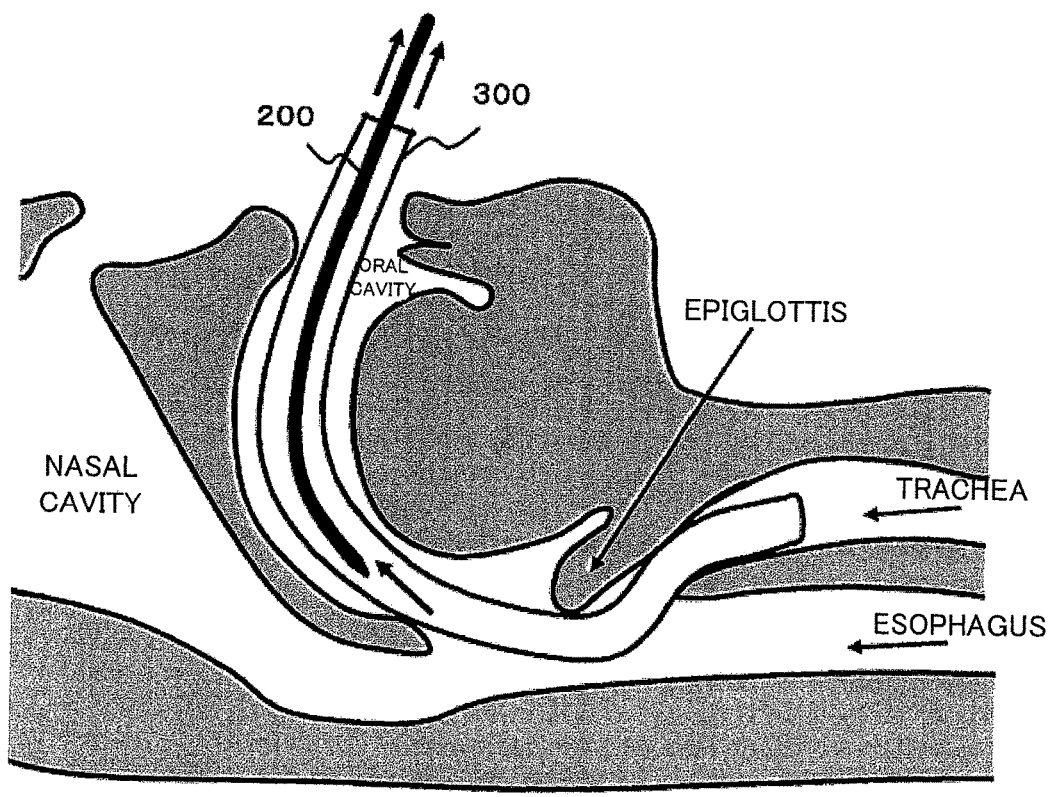
FIG. 18A is a diagram showing a state that the bronchial fiber is being pulled out.
Figure 18B:
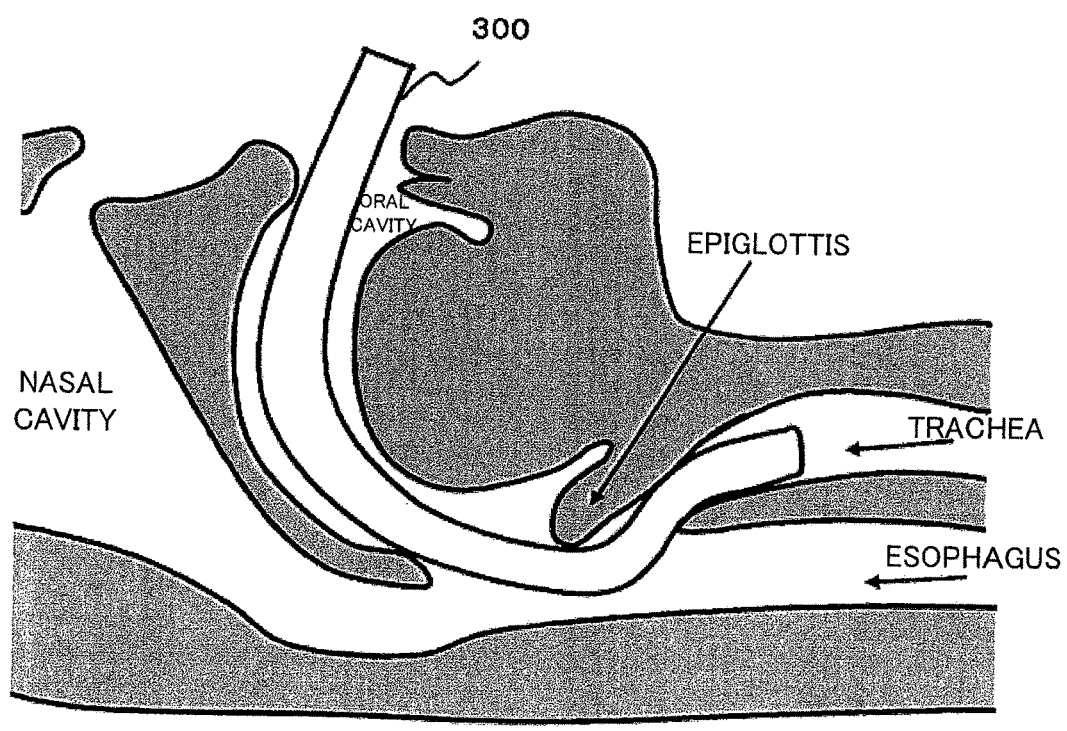
FIG. 18B is a diagram showing a state that the bronchial fiber has been pulled out completely.

Next, after the endotracheal tube 300 is placed in the trachea, the bronchial fiber 200 is removed from the inside of the trachea and from the endotracheal tube. FIG. 18A is a diagram showing a state that the bronchial fiber 200 is being pulled out. FIG. 18B is a diagram showing a state that the bronchial fiber 200 was pulled out completely. FIG. 18B shows a state of an accomplishment of endotracheal tube intubation treatment for securing airway.

The above described basic procedures for using the present endotracheal intubation support instrument 100.

The above described preferable embodiments of the present invention with diagrams. It should be understood various variations are possible within the technical scope of the present invention. Accordingly, the technical scope of the present invention should be limited only by wordings of attached claims.

It is possible to apply the present invention to an instrument for supporting endotracheal intubation that an endotracheal tube for artificial ventilation is reliably inserted into the trachea of the patient having the difficult airway.

Figure 19:
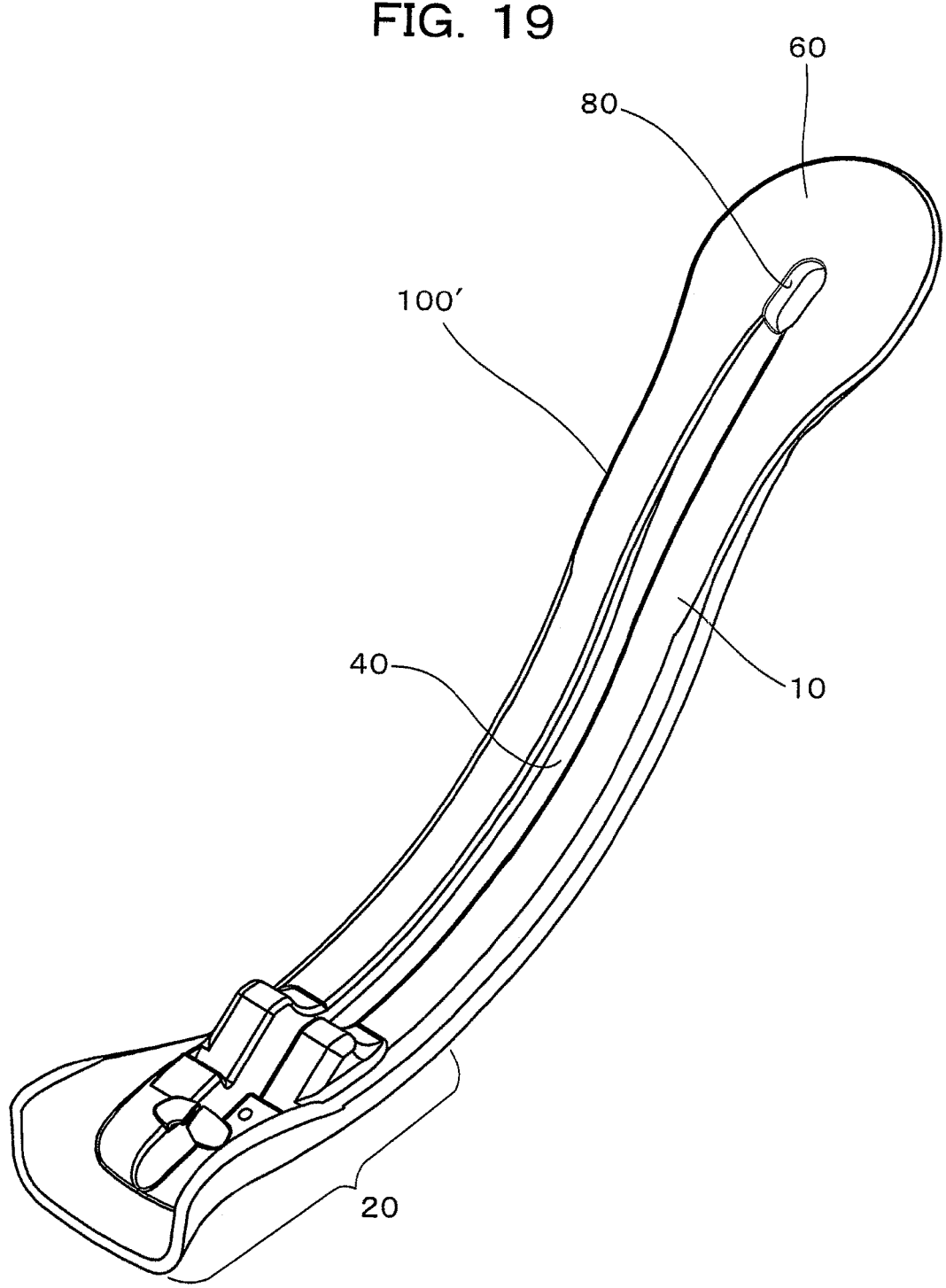
FIG. 19 is a front perspective view of the other embodiment of the endotracheal intubation support instrument of the present invention.
Figure 20B:
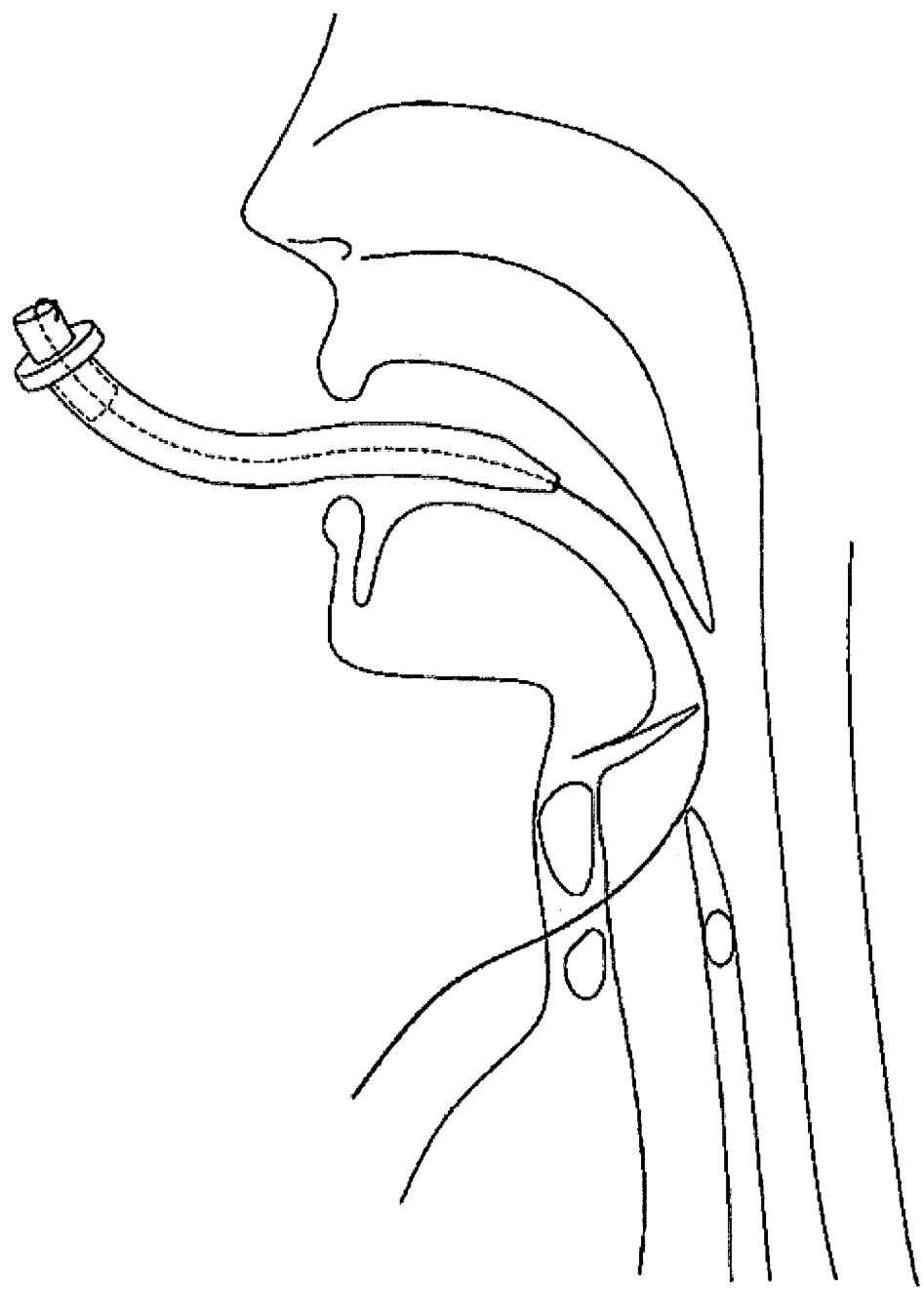
FIG. 20B is a diagram using FIG. 2 shown in JP-A-2003-235978 to explain procedure of retrograde endotracheal intubation.

It is possible to execute the present invention as the other embodiment shown in FIG. 19. The endotracheal intubation support instrument 100' shown in FIG. 19 comprises, as with the endotracheal intubation support instrument 100 in the mentioned embodiment, the main body section 10, the blade section 20, and the handle section 60. The handle section 60 of the endotracheal intubation support instrument 100' has a penetrating hole 80 which is formed at a vicinity of the center of the handle section 60, that is, on an extended line from the U-shaped groove 40. According to the embodiment shown in FIG. 19, in a case that the oxygen mask is put on a patient to whom the endotracheal intubation support instrument 100' is inserted, even if the handle section 60 is placed so that the handle section 60 covers a vent of the oxygen mask, it is possible to secure breathability by the penetrating hole 80 formed in the handle section 60. That is, it is possible to prevent by the handle section 60, the vent of the oxygen mask from being blocked. The penetrating hole 80 illustrated is just one example, and with respect to the penetrating hole 80, the position, size and number of pieces may be changed as appropriate.

The invention claimed is:

1. An endotracheal intubation support instrument for, prior to endotracheal intubation where an endotracheal tube is inserted from an oral cavity of a patient into a trachea, introducing and passing a bronchial fiber from the oral cavity into the trachea, comprising:

a main body section having flexibility;
a handle section and a blade section, the handle section extending from one end of the main body section and the blade section extending from another end of the main body section; and
a U-shaped groove being provided in such a way as to extend from the handle section to the blade section through the main body section, open from a central portion of a cross section of the U-shaped groove toward one side with respect to a short axial direction, and allow a flexible tube of the bronchial fiber to enter and exit the U-shaped groove freely, wherein
the blade section comprises a flap configured to subsume all or a part of a larynx of the patient and a lifting body having on a top of both banks of the U-shaped groove, a first protruding portion heaving in a mountain shape and a second protruding portion being provided closer to the main body section with respect to the first protruding portion in an insertion direction and heaving in another mountain shape,
the flap having walls smoothly extending toward a direction where the U-shaped groove opens from an end portion of a side surface of each side of the main body section, so that an outline of the blade section is in a concave shape, and
when the endotracheal intubation support instrument is in use, the U-shaped groove is located at a position facing the larynx of the patient, while the first protruding portion is configured to contact with a peripheral portion of an epiglottis of the patient, and the second protruding portion is configured to contact with a peripheral portion of a glossal root of the patient.

2. The endotracheal intubation support instrument according to claim 1, further comprising:

a bridge including: chips extending from the banks of the U-shaped groove toward a center respectively in an inside region of the flap; and a gap at a vicinity of a central portion formed by the chips facing each other, and providing under the bridge a cavity having a size allowing the bronchial fiber to pass through and being communicated with the U-shaped groove, wherein
the bridge has a structure such that: in a case that a vicinity of a tip of the bronchial fiber is put on an upper surface of the bridge, the bridge works as a placing stand; and in a case the bronchial fiber passes under a lower surface of the bridge to move ahead, the bronchial fiber lying under the bridge is allowed to spread out the chips because of the flexibility of the chips, and pass through the bridge from a lower side to an upper side to remove from the bridge.

3. The endotracheal intubation support instrument according to claim 2, wherein the gap located at the vicinity of the central portion between the chips, arranged in a right-left direction, constituting the bridge is provided obliquely to a center line of the U-shaped groove.

4. The endotracheal intubation support instrument according to claim 2, wherein coloring or mark is provided on either the blade section or the main body section, so that the tip of the bronchial fiber reaching a vicinity of the bridge of the blade section is viewed by an image of a finder, when the bronchial fiber is being inserted using the endotracheal intubation support instrument.

5. The endotracheal intubation support instrument according to claim 1, wherein the main body section is bent gently in a S-shape, the blade section is provided in such a way as to extend from an end of a side where an opening surface of the U-shaped groove of the main body section curves inward, and the handle section is provided in such a way as to extend from an end of a side where the opening surface of the U-shaped groove of the main body section curves outward.

6. The endotracheal intubation support instrument according to claim 1, wherein
the flap includes wall boards which raise from the end portion of the side surface of each side of the main body section and extend widely toward a tip of insertion in a trapezoidal shape, so as to subsume the larynx,
the main body section and an end of the flap are made of a smoothly continuing thin plate in an almost concave shape viewed from a front, and
a tip portion of the flap gently curls outward.

7. The endotracheal intubation support instrument according to claim 1, wherein
the lifting body has an incision, the incision being: allowed to take in a tip of a peripheral portion of the epiglottis; and provided between the first protruding portion and the second protruding portion, wherein
in a case the epiglottis blocks the trachea, by manipulation to the handle section to control a position of the blade section, the incision is allowed to catch and raise the tip of the epiglottis to open the epiglottis for establishing a viewing field toward the trachea.

8. The endotracheal intubation support instrument according to claim 1, wherein
the second protruding portion is higher than the first protruding portion.

9. The endotracheal intubation support instrument according to claim 1, including a suction passage sucking body fluid and having a first end opening in the flap of the blade section and a second end opening at the handle section, so that the suction passage runs through the flap, the main body section, and the handle section.

10. The endotracheal intubation support instrument according to claim 9, wherein
in a case that a suction tube is used as the suction passage, an engagement groove is provided for engaging with the suction tube.

11. The endotracheal intubation support instrument according to claim 1, wherein
fine roughness or at least one fine rib having a sharp top is provided on a surface of the U-shaped groove, in order to reduce friction resistance produced by contact of the bronchial fiber and the U-shaped groove.

12. The endotracheal intubation support instrument according to claim 1, wherein
a length and a shape of the endotracheal intubation support instrument are adjusted so that a back end of the handle section is located at a vicinity of outside of the oral cavity of the patient, and
a tip of the blade section is configured to be located at a vicinity of the epiglottis of the patient so that an oxygen mask can be put on the patient.

13. The endotracheal intubation support instrument according to claim 1, wherein
a thickness gets thinner from the main body section toward the handle section, and a thin portion is designed in such a way as to be easily bent and curled.

14. The endotracheal intubation support instrument according to claim 1, wherein
the handle section is designed in an elliptically spread shape for easy holding, and has a groove for folding on a back surface of the handle section.

15. An endotracheal intubation support instrument which is, prior to endotracheal intubation where an endotracheal tube is inserted from an oral cavity of a patient into a trachea, inserted to the oral cavity of the patient, the endotracheal intubation support instrument comprising:
a main body section having flexibility;
a blade section being provided at a forward end of the main body section in an insertion direction;
a handle section being provided at a rearward end of the main body section in the insertion direction; and
a U-shaped groove being provided in such a way as to extend from the handle section up to the blade section through the main body section, and open toward a front side of each of the main body section, the blade section, and the handle section, wherein
the blade section comprises:
a flap having a pair of side walls extending spacedly from both end portions with respect to a transverse direction of the U-shaped groove toward the front side; and
a lifting body being arranged at a position sandwiched by the pair of the side walls of the flap, and having a first protruding portion and a second protruding portion located next to a rearward portion of the first protruding portion in the insertion direction, the first protruding portion and the second protruding portion being provided on a top of both sides of the U-shaped groove in the transverse direction of the U-shaped groove.

16. The endotracheal intubation support instrument according to claim 15, further comprising a bridge arranged at a position sandwiched by the pair of side walls of the flap and provided in such a way as to traverse above the U-shaped groove, wherein
the bridge has a pair of chips extending from the both sides with respect to the traverse direction of the U-shaped groove respectively and facing each other above the U-shaped groove, and a gap is formed at a position where the pair of chips faces each other.

17. The endotracheal intubation support instrument according to claim 16, wherein
the gap is provided obliquely to a center line of the U-shaped groove.

18. The endotracheal intubation support instrument according to claim 15, wherein
the flap is designed so that a space between the pair of side walls expands gradually toward a forward portion of the flap in the insertion direction.

19. The endotracheal intubation support instrument according to claim 15, wherein
a penetrating hole penetrating the handle section is formed in the handle section.

* * * * *